United States Patent [19]

Gammill et al.

[11] Patent Number: 5,262,417
[45] Date of Patent: Nov. 16, 1993

[54] ANTIBACTERIAL QUINOLONE COMPOUNDS

[75] Inventors: Ronald B. Gammill, Portage; Sharon N. Bisaha, Lawton; Joseph M. Timko, Kalamazoo; Thomas M. Judge, Kalamazoo; Michael R. Barbachyn, Kalamazoo, all of Mich.; Kyoung S. Kim, Lawrenceville, N.J.

[73] Assignee: The Upjohn Company, Kalamazoo, Mich.

[21] Appl. No.: 679,069

[22] PCT Filed: Nov. 24, 1989

[86] PCT No.: PCT/US89/05213

§ 371 Date: Jun. 3, 1991

§ 102(e) Date: Jun. 3, 1991

[51] Int. Cl.$^5$ .................. A61K 31/495; C07D 401/04
[52] U.S. Cl. ...................................... 514/254; 544/349; 544/362; 544/363; 546/123; 546/156
[58] Field of Search ...................... 544/363; 514/254

[56] References Cited

U.S. PATENT DOCUMENTS

| | | | |
|---|---|---|---|
| 3,221,015 | 11/1965 | Cignarella | 260/268 |
| 3,590,036 | 6/1971 | Lesher et al. | 546/123 |
| 4,146,719 | 3/1979 | Irikura | 544/363 |
| 4,284,629 | 8/1981 | Grohe et al. | 424/246 |
| 4,341,784 | 7/1982 | Matsumoto et al. | 424/256 |
| 4,352,803 | 10/1982 | Matsumoto et al. | 424/251 |
| 4,359,578 | 11/1982 | Matsumoto et al. | 544/362 |
| 4,552,882 | 11/1985 | Soler | 546/123 |
| 4,556,658 | 12/1985 | Grohe et al. | 514/254 |
| 4,559,341 | 12/1985 | Petersen et al. | 514/254 |
| 4,559,342 | 12/1985 | Petersen et al. | 514/254 |
| 4,563,448 | 1/1986 | Petersen et al. | 514/187 |
| 4,571,396 | 2/1986 | Hutt et al. | 514/249 |
| 4,578,473 | 3/1986 | Domagala et al. | 546/156 |
| 4,588,726 | 5/1986 | Petersen et al. | 544/363 |
| 4,670,444 | 6/1987 | Grohe et al. | 514/300 |
| 4,705,788 | 11/1987 | Schriewer et al. | 514/254 |
| 4,795,751 | 1/1989 | Matsumoto et al. | 544/363 |
| 4,886,810 | 12/1989 | Matsumoto et al. | 544/363 |
| 4,973,590 | 11/1990 | Preiss et al. | 544/363 |
| 4,980,353 | 12/1990 | Grohe et al. | 544/363 |

FOREIGN PATENT DOCUMENTS

| | | |
|---|---|---|
| 0132845 | 2/1985 | European Pat. Off. . |
| 0153163 | 8/1985 | European Pat. Off. . |
| 3420743 | 12/1985 | Fed. Rep. of Germany . |
| WO88/02627 | 4/1988 | PCT Int'l Appl. . |
| 853954 | 5/1985 | South Africa . |
| 8504767 | 7/1985 | Spain . |
| 2160519 | 12/1985 | United Kingdom . |

OTHER PUBLICATIONS

R. Albrecht, Progress in Drug Research, 21, pp. 9–104 (1977).
Egawa et al., J. Med. Chem., 27, pp. 1543–1548 (1984).
M. P. Wentland and J. B. Cornett, Annual Reports in Medicinal Chemistry, 20, pp. 145–154 (1985).
D. Bouzard et al., J. Med. Chem., 32, pp. 537–542 (1989).
D. T. Chu et al., J. Med. Chem., 28, pp. 1558–1564 (1985).
D. T. Chu et al., J. Med. Chem., 29, pp. 2363–2369 (1986).
D. T. Chu et al., J. Med. Chem., 30, pp. 504–509 (1987).
K. B. Wiberg and V. Z. Williams, J. Org. Chem., 35, pp. 369–373 (1970).
D. E. Applequist et al., J. Org. Chem., 47, pp. 4985–4995 (1982).
Poster Abstract #962.
Poster Abstract #963.

*Primary Examiner*—C. Warren Ivy
*Assistant Examiner*—James H. Turnipseed
*Attorney, Agent, or Firm*—Donald L. Corneglio; Thomas A. Wootton

[57] ABSTRACT

A quinolone compound of Formula (I)

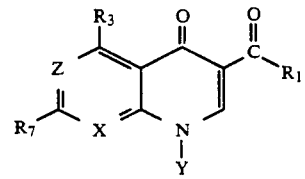

as defined herein having antibacteria properties, pharmaceutical compositions containing the quinoline compound and method for treating bacterial infections in animals including humans.

7 Claims, No Drawings

5,262,417

ANTIBACTERIAL QUINOLONE COMPOUNDS

This application is a continuation-in-part of PCT/US89/05213, filed Nov. 24, 1989, which was a continuation in part of three U.S. patent applications: U.S. Ser. No. 07/411,449, filed Sep. 25, 1989, abandoned, U.S. Ser. No. 07/355,016, filed May 22, 1989, abandoned and U.S. Ser. No. 07/335,163, filed Apr. 7, 1989, abandoned. U.S. Ser. No. 07/335,016 was a continuation in part of U.S. Ser. No. 07/326,907 filed Mar. 22, 1989 abandoned. U.S. Ser. No. 07/335,163 was a continuation in part of U.S. Ser. No. 07/280,603 filed Dec. 6, 1988 abandoned.

BACKGROUND OF THE INVENTION

The present invention relates to new quinolone compounds useful as antibacterial agents. Various quinolone type structures are known for their antibacterial properties, however new antibacterials are continually sought especially those which exhibit both gram positive and gram negative activity.

INFORMATION DISCLOSURE

International Application No. PCT/US87/02556 (International Publication No. WO 88/02627) discloses naphthyridine- and quinoline-carboxylic acids having a 1-tertiary-alkyl substituent, compositions containing them, and their use in treating bacterial infections in warm-blooded animals and man. 1-tertiary-alkyl substituents disclosed include 1,1-dimethylethyl, 1,1-dimethylpropyl, 1-methyl-1-phenylethyl, 1-phenylcyclopropyl, 2-methyl-1-phenylcyclopropyl, 1-methylcyclopropyl, 1,2-dimethylcyclopropyl, 1-methylcyclobutyl, 1-methylethenyl and 1-adamantyl. There are disclosed numerous N-heterocyclic ring substituents in the 7-position including piperazinyl, piperidinyl, 3-amino-1-pyrrolidinyl, 3-aminoalkyl-1-pyrrolidinyl, 2-aminoalkylmorpholin-4-yl, 2-aminoalkyl-thimorpholin-4-yl, and diazabicycloalkyl groups containing 7-9 atoms in the diazobicycloalkyl ring system. Also disclosed are amines and intermediates used in the preparation of the naphthyridine- and quinoline-carboxylic acids.

International Application No. PCT/US87/02556 (International Publication No. WO 88/02627) describes additional background references including:

R. Albrecht, Progress in Drug Research, 21:9-104 (1977); Egawa, et al., J. Med. Chem. 27:1543-1548 (1984); M. P. Wentland and J. B. Cornett, Annual Reports in Medicinal Chemistry, 20:145-154 (1985); U.S. Pat. Nos. 3,590,036, 4,146,719, 4,284,629, 4,341,784, 4,352,803, 4,359,578, 4,556,658, 4,559,341, 4,559,342, 4,563,448, 4,571,396, 4,578,473, and 4,705,788; German Offen. DE 3142854; GB A 2,160,519 and GB A 937,183; EP 0,132,845, EP 0,134,165, EP 0,153,163, EP 0,166,939, and EP 0,167,763; Spanish Patent 8504767; and South African Patent Application Publication No. 853954.

At the 28th ICAAC (Interscience Conference on Antimicrobial Agents and Chemotherapy) held Oct. 23-26, 1988 in Los Angeles, Calif. the antibacterial activity of 7-(1R,4R-2,5-diazabicyclo-[2,2,1]-heptan-2-yl)-6-fluoro-1-t-butyl-1,4-dihydro-4-oxo-1,8-naphthyridine-3-carboxylic acid (BMY 40062) was disclosed in poster abstracts (#962 and #963). The synthesis and structure-activity relationships of related quinoline and naphthyridine carboxylic acids incorporating 1-tertiary-alkyl substituents is described by D. Bouzard, et al., in J. Med. Chem. 32:537-542 (1989).

The synthesis and structure-activity relationships of various 1-aryl-6-fluoroquinolone, 1-aryl-6-fluoronaphthyridine and 1-aryl-6,8-difluoroquinolone antibacterial agents is described by D. T. Chu, et al., in J. Med. Chem. 28:1558-1564 (1985); J. Med. Chem. 29:2363-2369 (1986); and J. Med Chem. 30:504-509 (1987).

The synthesis of a variety of 1- and 2-substituted bicyclo[1.1.1]pentanes is described by K. B. Wiberg and V. Z. Williams in J. Org. Chem., 35:369-373 (1970).

The synthesis of a variety of 1,3-disubstituted bicyclo[1.1.1]pentanes is described by D. E. Applequist, et al., in J. Org. Chem. 47:4985-4995 (1982).

Various quinolone-carboxylic acids are disclosed in U.S. Pat. No. 4,563,448 for combating plant-pathogenic bacteria. Other quinolone acids suitable for treating bacteria infection are disclosed in U.S. Pat. No. 4,559,342 and in German Patent DE 3,615,303. In one aspect the present compounds, Formual IA also exhibit antibacteria properties but unlike the disclosed compounds possess a unique substituent on the piperazinyl ring.

The preparation of various piperazinyl and 3-amino-1-pyrrolidinyl naphthyridine derivatives, including 2-(4-(1-cyclopropyl-3-carboxy-6-fluoro-1,4-dihydro-4-oxo-7-quinolinyl)-1-piperazinyl)-2-butanedioic acid, 2-(4-(1-cyclopropyl-3-carboxyethyl-6-fluoro-1,4-dihydro-4-oxo-7-quinolinyl)-1-piperazinyl)-2-butanedioic acid, dimethyl ester, 2-(4-(1-ethyl-3-carboxy-6-fluoro-1,4-dihydro-4-oxo-7-quinolinyl)-1-piperazinyl)-2-butanedioic acid, and 2-(4-(1-ethyl-3-carboxyethyl-6-fluoro-1,4-dihydro-4-oxo-7-quinolinyl)-1-piperazinyl)-2-butanedioic acid, dimethyl ester are disclosed in Japanese publication 62-207258 (Chem. Abst. 108(15):131600s) and Great Britain Patent Application 87-GB-002508.

SUMMARY OF THE INVENTION

The present invention is directed toward new compounds, generically represented by Formula I, useful as antibacterials or in the preparation of antibacterial compositions. Formula I is defined where X is nitrogen, a carbon substituted with a hydrogen, hydroxyl, cyano, nitro, halogen $C_1$-$C_4$ alkyl or an amine; $R_3$ is H, halogen, amine or hydroxy; Y is 1) $C_1$-$C_{10}$ alkyl, $C_3$-$C_{10}$ cycloalkyl or heterocycloalkyl, phenyl or substituted phenyl wherein the substituent is one or more of $C_1$-$C_{10}$ alkyl, halogen, hydroxyl, hydrogen or a combination thereof, or $C_2$-$C_4$ alkylene wherein each carbon may be substituted with a fluorine;

2) —$C(R_{13})_2C$=$CR_{14}$ where $R_{13}$ is independently hydrogen, methyl, halogen substituted methyl or joined to form a cyclopropyl and $R_{14}$ is hydrogen, fluorine, chlorine, bromine, $C_1$-$C_6$ alkyl or phenyl; or 3) bicyclo (1.1.1) pent-1-yl which can be substituted at C-3 with $C_1$-$C_6$ alkyl, $C_1$-$C_6$ alkoxy, fluoro, bromo, chloro, nitro, amino, hydroxy, COOH, COO($C_1$-$C_6$ alkyl) and phenyl optionally substituted with one or two $C_1$-$C_4$ alkyl, $C_1$-$C_3$ alkoxy, halo, trifuromethyl, $C_2$-$C_6$ dialkylamino, $C_1$-$C_3$ alkylthio or nitro;

Z is nitrogen, or a fluorine substituted carbon; wherein $R_1$ is hydrogen or hydroxyl; wherein $R_7$ is selected from the Formula A'-H'; wherein $R^2$ is independently selected from H, $C_3$-$C_6$ cycloalkyl, $C_5$-$C_6$ cycloalkenyl, —Q—N($R_{10}$)—C($R_9$)H—CH$_2$—C($R_8$)O, —Q—N($R_{10}$)—C($R_9$)=CH($R_{12}$)—C($R_8$)O, $R_8$ is hydrogen, hydroxyl, amine, $C_1$-$C_4$ alkoxy or aryloxy,—SH, $C_1$-$C_6$ thioalkyl or thioaryl; $R_9$ is $C_1$-$C_4$ alkyl, $C_6$-$C_{12}$ aryl, alkylaryl, heteroaryl, —$(CH_2)_n$—$CO_2$—$(CH_2)_m$—$R_{11}$, $R_{11}$ is hydrogen, hydroxyl, methyl, alkyloxy, aryloxy or an amine, n is 0–4 and m is 0–4; $R_{10}$ is hydrogen, —$(CH_3)_o$, $C_2$-$C_4$ alkyl, $C_6$-$C_{12}$ aryl, alkylaryl, heteroaryl, or acetyl, where o is 0 or 1; Q is $(CH_2)_q$ where q is 0–2, CH—$CH_3$ or C$(CH_3)_2$ and $C_1$-$C_6$ alkyl optionally substituted with 1, 2 or 3 hydroxy, fluoro, chloro, amino, $C_1$-$C_4$ alkylamino, trifluoroacetylamino and phenyl; $A_1$, $A_2$, $A_3$ and $A_4$ are independently selected from H, amino, hydroxy, halogen, $C_1$-$C_4$ alkyl optionally substituted with 1, 2 or 3 hydroxy, fluoro, chloro, amino, $c_2$-$C_4$ alkylene, ethynyl, $C_1$-$C_4$ alkylamino, trifluoroacetylamino, $C_3$-$C_6$ cycloalkyl, $C_1$-$C_{18}$ alkoxymethyl, phenoxymethyl, $C_1$-$C_3$ alkyl aminomethyl, $C_1$-$C_3$ dialkyl aminomethyl, $C_6$-$C_{12}$ aryl, substituted aryl, heteroaryl or substituted heteroaryl containing at least one O, N or S and phenyl; and pharmaceutically acceptable acid addition and base salts thereof.

In one aspect, the compound of the present invention is as shown in Formula IA or therapeutically acceptable salts wherein:

$R_1$ is hydrogen or hydroxyl;

Y is $C_1$-$C_{10}$ alkyls, $C_3$-$C_{10}$ cycloalkyl or heterocycloalkyl, a phenyl, or a substituted phenyl wherein the substituent on the phenyl group is one or more of $C_1$-$C_{10}$ alkyl, halogen, hydroxyl, hydrogen or a combination thereof, or $C_2$-$C_4$ alkylene wherein each carbon atom may be substituted with fluorine;

$R_3$ is hydrogen, halogen, amine or hydroxyl;

$A_1$, $A_2$, $A_3$, $A_4$ are independently hydrogen, hydroxyl, halogen, $C_1$-$C_4$ alkyl, ethenyl, ethynyl, $C_3$-$C_6$ cycloalkyl, fluoromethyl, difluoromethyl, difluoroethyl, trifluoromethyl, hydroxymethyl, $C_1$-$C_{18}$ alkoxy methyl, phenoxymethyl, $C_1$-$C_3$ alkyl aminomethyl, $C_1$-$C_3$ dialkyl aminomethyl, $C_6$-$C_{12}$ aryl, substituted aryl, heteroaryl or substituted heteroaryl containing at least one O, N or S;

$R_8$ is hydrogen, hydroxyl, amine, $C_1$-$C_4$ alkoxy or aryloxy, —SH, $C_1$-$C_6$ thioalkyl or thioaryl;

$R_9$ is $C_1$-$C_4$ alkyl, $C_6$-$C_{12}$ aryl, alkylaryl, heteroaryl, —$(CH_2)_n$—$CO_2$—$(CH_2)_m$—$R_{11}$, wherein $R_{11}$ is hydrogen, hydroxyl, methyl, alkyloxy, aryloxy or an amine, n is 0–4 and m is 0–4;

$R_{10}$ is hydrogen, —$(CH_3)_o$, $C_2$-$C_4$ alkyl, $C_6$-$C_{12}$ aryl, alkylaryl, heteroaryl, or acetyl, where o is 0 or 1;

$R_{12}$ is hydrogen, CN, halogen, or $R_9$;

Z is nitrogen or carbon substituted by fluorine;

X is nitorgen, a carbon substituted with hydrogen, hydroxyl, cyano, nitro, halogen, $C_1$-$C_4$ alkyl, or an amine; and Q is $(CH_2)_q$ where q is 0–2, CH—$CH_3$ or C$(CH_3)_2$.

The dotted bonds indicate that the carbon atom having the $A_1$ group can be bonded to either the nitrogen to form Formula IA$_2$ or the carbon atom having the $A_4$ group to form Formula IA$_b$. When the structure is as depicted in Formula IA$_a$ then $R_{10}$ is —$(CH_3)_o$ where o is 0 and preferably, Q is $(CH_2)_q$ where q is 0.

Preferred compounds of the Formula IA structure can include 2-[4-(1-Cyclopropyl-3-carboxyl-6,8-difluoro-1,4-dihydro-4-oxo-7-quinolinyl)-1-piperazinyl]2-butenedioic acid, dimethyl ester; 2-[4-(1-Ethyl-3-carboxy-6-fluoro-1,4-dihydro-4-oxo-7-quinolinyl)-1-piperizinyl]2-butenedioic acid, dimethyl ester; 2-[4-(1-Cyclopropyl-3-carboxy-5,6,8-trifluoro-1,4-dihydro-4-oxo-7-quinolinyl)-1-piperazinyl]2-butenedioic acid, dimethyl ester; 2-[4-(1-Cyclopropyl-3-carboxy-6-fluoro-1,4-dihydro-4-oxo-7-quinolinyl)-1-piperazinyl]2-butenedioic acid, dimethyl ester; and (E)-2-(N-(3-carboxyl-1-cyclopropyl-6,8-difluoro-1,4-dihydro-4-oxo-7-quinolinyl)-1-(3-aminopyrrolinyl))-2-butenedioic acid, 1,4-dimethyl ester.

In another aspect, the present invention is as shown in Formula IB which are novel 4-oxo-naphthyridine- and 4-oxo-quinoline-3-carboxylic acids derivatives having a 1-bicyclo[1.1.1]pent-1-yl substituent, to compositions containing the same, and their use in treating bacterial infections in warm-blooded animals and man. Also disclosed are novel amines and intermediates used in the preparation of the same.

In yet another aspect, the subject invention is novel naphthyridine- and quinoline-carboxylic acids derivatives having a propargyl moiety (RC≡C—CR'$_2$—) at the Y position according to Formula I, as structurally depicted in Formula IC and to compositions containing the same.

In another aspect, the present invention is a pharmaceutical composition containing an antibacterially effective amount of a compound or therapeutically acceptable salts thereof according to Formula I in admixture with a pharmaceutical carrier. The composition can contain from about 0.5 to about 90% by weight of such compound. The composition can be present in unit dose form of tablets, pills, dragees, capsules, ampules or suppositories.

In yet another aspect, the present invention is method for treating bacterial infection in animals including humans which comprises administering an antibacterially effective amount of a compound or therapeutically acceptable salts thereof according to Formula I. In the method the compound can be administered orally or parenterally.

DETAILED DESCRIPTION OF INVENTION

The present invention relates to quinolone compounds and antibacterial agents containing these compounds. The quinolone compounds are structurally represented by Formula I, shown on the Formula Sheet, and includes therapeutically acceptable salts thereof. Formula I is further broken down into Formula IA, IB and IC where each structure encompasses a similar heterocyclic ring structure each with a particular Y substituent. For instance, Formula IA has a group of alkyl, alkylene, cycloalkyl, heterocycloalkyl phenyl and substituted phenyls at the Y position, Formula IB has a bicyclo (1.1.1) pent-1-yl substituent at the Y position and Formula IC has a propargyl substituent at the Y position.

Formula IA

Formula IA is defined wherein $R_1$ is hydrogen or hydroxyl; Y is $C_1$-$C_{10}$ alkyls, $C_3$-$C_{10}$ cycloalkyl or heterocycloalkyl, a phenyl, or a substituted phenyl wherein the substituent on the phenyl group is one or more of $C_1$-$C_{10}$ alkyl, halogen, hydroxyl, hydrogen or a combination thereof, or $C_2$-$C_4$ alkylene wherein each carbon atom may be substituted with fluorine (known substituents for the Y group are described by Domagala et al., J. Med. Chem., 31, 991 (1988) herein incorporated by reference); $R_3$ is hydrogen, halogen, amine or hydroxyl; $A_1$, $A_2$, $A_3$, $A_4$ are independently hydrogen, hydroxyl, halogen, $C_1$-$C_4$ alkyl, ethenyl, ethynyl, $C_3$-$C_6$ cycloalkyl, fluoromethyl, difluoromethyl, difluoroethyl, trifluoromethyl, hydroxymethyl, $C_1$-$C_{18}$ alkoxy methyl, phenoxy-methyl, $C_1$-$C_3$ alkyl aminomethyl, $C_1C_3$ dialkyl aminomethyl, $C_6$-$C_{12}$ aryl, substituted aryl, heteroaryl or substituted heteroaryl; $R_8$ is hydrogen, hydroxyl, amine, $C_1$-$C_4$ alkoxy or aryloxy, —SH, $C_1$-$C_6$ thioalkyl or thioaryl; $R_9$ is $C_1$-$C_4$ alkyl, $C_6$-$C_{12}$ aryl, alkylaryl, heteroaryl, —$(CH_2)_n$—$CO_2(CH_2)_m$—$R_{11}$, wherein $R_{11}$ is hydrogen, hydroxyl, methyl, alkyloxy, aryloxy or an amine, n is 0-4 and m is 0-4; $R_{10}$ is hydrogen, —$(CH_3)_o$, $C_2$-$C_4$ alkyl, $C_6$-$C_{12}$ aryl, alkylaryl, heteroaryl, or acetyl, where o is 0 or 1; $R_{12}$ is hydrogen, CN, halogen, or $R_9$; Z is nitrogen or carbon substituted by fluroine; X is nitrogen, a carbon substituted with hydrogen, hydroxyl, cyano, nitro, halogen, $C_1$-$C_4$ alkyl, or an amine; and Q is $(CH_2)_q$ where q is 0-2, CH—$CH_3$ or $C(CH_3)_2$.

The dotted bonds indicate that the carbon atom having the $A_1$ group can be boned to either the nitrogen to form Formula IAa or the carbon atom having the $A_4$ group to form Formula IAb. When the structure is as depicted in Formula IAa then $R_{10}$ is —$(CH_3)_o$ where o is 0 and preferably, Q is $(CH_2)_q$ where q is 0.

Preferred quinolone compounds of Formula IAa are where $R_1$ is hydroxy, Y is cyclopropane or ethyl, $R_3$ is hydrogen or fluorine, Z and X are carbon or fluorine substituted carbon, $A_1$, $A_2$, $A_3$, and $A_4$ are hydrogen, $R_8$ is methoxyl, $R_9$ is a carbomethoxyl ester so as to form either the dimethylester of maleic or fumaric acid and $R_{10}$ is— $(CH_3)_o$ where o is 0. Preferred quinolone compounds of Formula IAb are when $R_1$ is hydroxyl and Y is cyclopropyl and $R_3$, $A_1$, $A_2$, $A_3$, $A_4$ and $R_{11}$ are hydrogen, $R_8$ is O—$CH_3$, $R_9$ is $C(O)OCH_3$, Z and X are C(F) and Q is $(CH_2)_q$ where q is zero.

Examples of "$C_1$-$C_{10}$ alkyl" are one to ten carbon atoms such as methyl, ethyl, propyl, butyl, etc. and isomeric forms thereof. The "$C_2$-$C_4$ alkylenes" are ethylene, propylene and 1 or 2-butylene and isomeric forms thereof. Examples of "$C_3$-$C_{10}$ cycloalkyl" are cyclopropyl, cyclobutyl, cyclopentyl, cyclohexyl, etc. and "heterocycloalkyl" are cycloalkyl ring which contrain at least one heteroatom such as oxygen, sulfur or nitrogen.

Examples of "$C_6$-$C_{12}$ aryl" are compounds such as phenyl, α-naphthyl, β-naphthyl, m-methylphenyl, p-trifluoromethylphenyl and the like. The aryl groups can also be substituted with one to 3 hydroxy, $C_1$-$C_3$ alkoxy, $C_1$-$C_3$ alkyl, trifluoromethyl, fluoro, chloro or bromo groups. Examples of "alkylaryl" are alkyl chains of one to eight carbon atoms and isomeric forms thereof which are substituted with aryl groups of 6 to 12 carbon atoms. Examples of "heteroaryls" are 6 to 12 carbon atom aryls which contain at least one heteroatom such as nitrogen, sulfur and oxygen.

An "amine" is meant to include primary, secondary and tertiary amines. "Halogen" is meant to include F, Cl, Br and I. "Therapeutically acceptable salts" are those compounds of Formula I wherein a carboxyl group is substituted with a counter ion such as Li, Na, K, Ca or other acceptable counter ions for carboxylic acids.

A generic scheme for the preparation of the Formula IAa quinolone compounds is illustrated in scheme 1, below. The scheme shows two alternative routes to arrive at the compound represented by formula IAa. Starting material "a" is converted to an enol-ether "b" which is treated with a primary amine to yield "c" which is treated with a base to yield "d" which is reacted with piperazine to yield "e" which is treated with dimethyl acetylene dicarboxalate to yield "f" which is hydrolyzed to yield "I". Alternatively, "d" is hydrolyzed to "h" which is treated with piperazine to yield "i" which is treated with dimethylacetylene dicarboxalate to yield "IAa".

A generic scheme for the preparation of the Formula IAb quinolone compounds is illustrated in Scheme 2, below. The chemistry is described by Domagala et al., J. Med. Chem., 31, 991 (1988).

The compounds according to the invention have good actions against Gram-positive and Gram-negative bacteria, particularly against enterobacteriaceae.

The effectiveness of the subject compounds on bacteria were obtained by performing a dip disk assay. The antibacterial activity of the compounds was determined by the disk-diffusion method. Paper disks (12.7 mm) were loaded with 0.05 ml of drug solution prepared at a concentration of 0.1 mcg/ml; the disks were allowed to air dry. They were then applied to the surface of microorganism-seeded agar assay trays, which contained the bacterial strain *Pseudomonas aeruginosa* UC 95 (PA), *Escherichia coli* UC 51 (EC), *Klebsiella pneumoniae* UC 57 (KP), or *Staphylococcus aureus* UC 80 (SA). The assay trays were incubated overnight under aerobic condition to allow for the growth of the organisms. Zones of growth inhibition due to the action of the antibiotic were then measured to the nearest millimeter.

| Formula IAa | (Growth Inhibition at 0.1 mcg/ml for) | | | |
|---|---|---|---|---|
| Compound | EC | PA | SA | KP |
| 1 | 31 | 36 | 27 | 31 |
| 2 | 23 | 25 | 21 | 25 |
| 3 | 29 | 36 | 25 | 29 |
| 4 (85568) | 27 | 33 | 28 | 33 |
| Ciprofloxacin | 29 | 38 | 27 | 31 |

The results show that compounds 1-4, all of Formula IAa, corresponding to Examples 1-4, below, have potent gram negative and positive activity as compared to the commercially available antibacteria Ciprofloxacin, from Miles Pharm. Div., West Haven, Conn.

The effectiveness of additional compounds 5-9, (5-7 are Formula IAa compounds and 8 and 9 are Formula IAb compounds) on bacteria were obtained by performing a dip disk assay as described above. The antibacterial activity of the compounds was determined by the disk-diffusion method where the disks were loaded with 0.05 ml of drug solution prepared at a concentration of 1.0 mcg/ml; the disks were allowed to air dry.

| | (Growth Inhibition at 1.0 mcg/ml for) | | | |
|---|---|---|---|---|
| Compound | EC | PA | SA | KP |
| 5 | 24 | 27 | 27 | 28 |
| 6 | 24 | 16 | 22 | 26 |
| 7 | 24 | 15 | 22 | 26 |
| 8 | 30 | 28 | 32 | 34 |
| 9 | 24 | 32 | 23 | 26 |

Compound 10 corresponding to Formula IAb and as described in Example 10 was compared to a control of ciprofloxacin as shown below.

| | Concentration in μg/ml | |
|---|---|---|
| Organism | Ciprofloxacin | Compound 10 |
| *Staphylococcus Aureus* | 0.25 | 0.03 |
| *Staphylococcus Aureus* | 1.0 | 0.06 |

-continued

| Organism | Concentration in µg/ml | |
|---|---|---|
| | Ciprofloxacin | Compound 10 |
| *Staphylococcus Aureus* | 0.5 | 0.06 |
| *Staphylococcus Aureus* | 0.5 | 0.06 |
| *Staphylococcus Epidermidis* | 0.125 | 0.03 |
| *Staphylococcus Faecalis* | 0.5 | 0.125 |
| *Staphylococcus Pneumoniae* | 0.05 | 0.06 |
| *Staphylococcus Pyogenes* | 0.25 | 0.06 |
| *Acinetobacter Calcoaceticus* | 0.25 | 0.03 |
| *Citrobacter Freundii* | 0.008 | 0.008 |
| *Enterobacter Cloacae* | 0.095 | 0.008 |
| *Escherichia Coli* | 0.015 | 0.008 |
| *Escherichia Coli* | 0.015 | 0.008 |
| *Escherichia Coli* | 0.015 | 0.008 |
| *Escherichia Coli* | 0.015 | 0.008 |
| *Klebsiella Pneumoniae* | 0.03 | 0.015 |
| *Proteus Penneri* | 0.03 | 0.03 |
| *Pseudomonas Aeruginosa* | 0.5 | 0.25 |
| *Pseudomonas Aeruginosa* | 0.25 | 0.125 |
| *Pseudomonas Aeruginosa* | 0.125 | 0.125 |
| *Serratia Marcescens* | 0.06 | 0.06 |

The data shows that compound 10, Example 10, had gram negative and positive activity greatly increased over that of ciprofloxacin.

Formula IB

Formula IB is defined wherein X is selected from N, CH, CF, CCl, CBr, and CCH$_3$;

wherein R$_3$ is selected from H, F and NH$_2$;

wherein R is selected from H, C$_1$-C$_6$ alkyl, C$_1$-C$_6$ alkoxy, fluoro, bromo, chloro, nitro, amino, hydroxy, COOH, COO(C$_1$-C$_6$ alkyl) and phenyl optionally substituted with one or two C$_1$-C$_4$ alkyl, C$_1$-C$_3$ alkoxy, halo, trifluromethyl, C$_1$-C$_6$ dialkylamino, C$_1$-C$_3$ alkylthio or nitro;

wherein R$_7$ is selected from Formula A', B', C', D', E', F', G' and H' (see GENERAL FORMULA sheet), wherein R$^2$ is independently selected from H, C$_3$-C$_6$ cycloalkyl, C$_5$-C$_6$ cycloalkenyl, —Q—N(R$_{10}$)—C(R$_9$)H—CH$_2$—C(R$_8$)O (see GENERAL FORMULA sheet) —Q—N(R$_{10}$)—C(R$_9$)=CH—C(R$_8$)O and C$_1$-C$_6$ alkyl optionally substituted with 1, 2 or 3 hydroxy, fluoro, chloro, amino, C$_1$-C$_4$ alkylamino, trifluoroacetylamino and pheny; wherein A$_1$A$_2$, A$_3$, and A$_4$ are independently selected from H, amino, hydroxyl, fluoro, chloro, C$_1$-C$_4$ alkyl optionally substituted with 1, 2 or 3 hydroxy, fluoro, chloro, amino, C$_2$-C$_4$ alkylene, C$_1$-C$_4$ alkylamino, trifluoroacetylamino and phenyl; and wherein n, when present, is selected from the integers 0, 1, 2, and 3;

R$_8$ is hydrogen or methyl;

R$_9$ is C$_1$-C$_4$ alkyl or —CH$_2$)$_m$—CO$_2$—(CH$_2$)$_p$—R$_{13}$, wherein R$_{13}$ is hydrogen, methyl or an amine, m is 0–4 and p is 0–4;

R$_{10}$ is hydroxy, amine, C$_1$-C$_4$ alkoxy or aryloxy; and Q is (CH$_2$)$_q$ is 0–2, CH—CH$_3$ or C(CH$_3$)$_2$;

pharmaceutically acceptable acid addition and base salts thereof.

R is preferably hydrogen.

R$_3$ is preferably hydrogen or NH$_2$.

X is preferably CH, CF and N.

R$_7$ is preferably 1-piperazinyl, 4-methyl-1-piperazinyl, 3-methyl-1-piperazinyl, 3,5-dimethyl-1-piperazinyl, 2,5-diazabicyclo [2,2,1]heptan-2-yl, 3-amino-1-pyrrolidinyl, 3-amino-4-methyl-1-pyrrolidinyl, 3-hydroxy-1-pyrrolidinyl and 3-ethylamino)methyl-1-pyrrolidinyl.

R$_{10}$ is preferably hydrogen.

R$_9$ is preferably a carbomethoxy ester and R$_8$ is methoxy so as to form either the dimethyl ester of succinic, maleic and/or fumaric acid.

Examples of "C$_1$-C$_4$ alkyl" are one to four carbon atoms such as methyl, ethyl, propyl, butyl and isomeric forms thereof. Examples of "C$_1$-C$_6$ alkoxy" include methoxy, ethoxy, propoxy, butoxy, heptoxy and isomeric forms thereof.

Examples of "C$_3$-C$_6$ cycloalkyl" are cyclopropyl, cyclobutyl, cyclopentyl and cyclohexyl. Examples of "C$_5$-C$_6$ cycloalkenyl" include cyclopenten-3-yl and cyclohexen-3-yl.

Examples of Formula IB compounds of this invention include:

1-(bicyclo[1.1.1]pent-1-yl)-6,8-difluoro-1,4-dihydro-4-oxo-7-(1-piperazinyl)-3-quinolinecarboxylic acid (Cpd #1);

1-(bicyclo[1.1.1]pent-1-yl)-1,4-dihydro-6-fluoro-4-oxo-7-(1-piperazinyl)-3-quinolinecarboxylic acid (Cpd #2);

1-(bicyclo[1.1.1]pent-1-yl)-1,4-dihydro-6-fluoro-7-(1-piperazin-yl)-4-oxo-3-quinolinecarboxylic acid, methane sulfonate;

7-[4-(cyclopenten-3-yl)-1-piperazinyl]-1-(bicyclo[1.1.1]pent-1-yl)-1,4-dihydro-6-fluoro-4-oxo-3-quinolinecarboxylic acid, hydrochloride;

7-(8-methyl-3,8-diazabicyclo[3.2.1]octan-3-yl)-1-(bicyclo-[1.1.1]pent-1-yl)-1,4-dihydro-6-fluoro-4-oxo-3-quinolinecarboxylic acid, hydrochloride;

7-[3-phenyl-1-piperazinyl]-1-(bicyclo[1.1.1]pent-1-yl)-1,4-dihydro-6-fluoro-4-oxo-3-quinolinecarboxylic acid, methanesulfonate;

1-(bicyclo[1.1.1]pent-1-yl)-1,4-dihydro-6-fluoro-7-(4-methyl-1-piperazinyl)-4-oxo-3-quinolinecarboxylic acid, hydrochloride;

7-(2,5-diazabicyclo[2.2.2]octan-2-yl)-1-(bicyclo[1.1.1]pent-1-yl)-1,4-dihydro-6-fluoro-4-oxo-3-quinolinecarboxylic acid;

7-(1S,4S-2,5-diazabicyclo[2.2.1]heptan-2-yl)-1-(bicyclo[1.1.1]pent-1-yl)-1,4-dihydro-6-fluoro-4-oxo-3-quinolinecarboxylic acid;

7-(3-aminomethyl)-1-pyrrolidinyl)-1-(bicyclo[1.1.1]pent-1-yl)-1,4-dihydro-6-fluoro-4-oxo-3-quinolinecarboxylic acid;

7-(3-(ethylamino)methyl-1-pyrrolidinyl-1-(bicyclo[1.1.1]pent-1-yl)-1,4-dihydro-6-fluoro-4-oxo-3-quinolinecarboxylic acid;

7-(3-methyl-1-piperazinyl)-1-(bicyclo[1.1.1]pent-1-yl)-1,4-dihydro-6-fluoro-4-oxo-3-quinolinecarboxylic acid;

7-(3,5-dimethyl-1-piperazinyl)-1-(bicyclo[1.1.1]pent-1-yl)-1,4-dihydro-6-fluoro-4-oxo-3-quinolinecarboxylic acid;

7-(4-(1,1-dimethylamino)-1-piperazinyl)-1-(bicyclo[1.1.1]pent-1-yl)-1,4-dihydro-6-fluoro-4-oxo-3-quinolinecarboxylic acid;

7-(4-(1,1-dimethylethyl)-1-piperazinyl)-1-(bicyclo[1.1.1]pent-1-yl)-1,4-dihydro-6-fluoro-4-oxo-3-quinolinecarboxylic acid;

7-(3-(ethylamino)methyl-1-pyrrolidinyl)-1-(bicyclo[1.1.1]pent-1-yl)-1,4-dihydro-6,8-difluoro-4-oxo-3-quinolinecarboxylic acid;

7-(3-amino-1-pyrrolidinyl)-1-(bicyclo[1.1.1]pent-1-yl)-1,4-dihydro- dihydro-6-fluoro-4-oxo-3-quinolinecarboxylic acid, hydrochloride;

7-(3-hydroxy-1-pyrrolidinyl)-1-(bicyclo[1.1.1]pent-1-yl)-1,4-dihydro-6-fluoro-4-oxo-3-quinolinecarboxylic acid;

7-(3-amino-1-pyrrolidinyl)-1-(bicyclo[1.1.1]pent-1-yl)-1,4-dihydro-6-fluoro-4-oxo-3-quinolinecarboxylic acid;

7-(3-amino-4-methyl-pyrrolidin-1-yl)-1-(bicyclo[1.1.1]pent-1-yl)-1,4-dihydro-6-fluoro-4-oxo-3-quinolinecarboxylic acid;

7-(3-hydroxy-1-pyrrolidinyl)-1-(bicyclo[1.1.1]pent-1-yl)-1,4-dihydro-6,8-difluoro-4-oxo-3-quinolinecarboxylic acid (Cpd #3);

7-(3-amino-4methyl-pyrrolidin-1-yl)-1-(bicyclo[1.1.1]pent-1-yl)-1,4-dihydro-6,8-difluoro-4-oxo-3quinolinecarboxylic acid;

7-(3-hydroxy-3-methylpyrrolidin-1-yl)-1-(bicyclo[1.1.1]pent-1-yl)-1,4-dihydro-6-fluoro-4-oxo-1,8-naphthyridine-3-carboxylic acid;

7-(3-amino-3-methylpyrrolidin-1-yl)-1-(bicyclo[1.1.1]pent-1-yl)-1,4-dihydro-6-fluoro-4-oxo-1,8-naphthyridine-3-carboxylic acid;

7-(3-hydroxy-3-phenylpyrrolidin-1-yl)-1-(bicyclo[1.1.1]pent-1-yl)-1,4-dihydro-6fluoro-4-oxo-1,8-naphthyridine-3-carboxylic acid;

7-(3-amino-3-phenylpyrrolidin-1-yl)-1-yl)-1-(bicyclo[1.1.1]pent-1-yl)-1,4-dihydro-6-fluoro-4-oxo-1,8-naphthyridine-3-carboxylic acid;

7-(3,5-dimethyl-1-piperazinyl)-1-(bicyclo[1.1.1]pent-1-yl)-1,4-dihydro-6-fluoro-4-oxo-1,8-naphthyridine-3-carboxylic acid;

7-(3-hydroxy-1-pyrrolidinyl)-1-(bicyclo[1.1.1]pent-1-yl)-1,4-dihydro-6-fluoro-4-oxo-1,8-naphthyridine-3-carboxylic acid (Cpd #91);

7-(1-piperazinyl)-1-(bicyclo[1.1.1]pent-1-yl)-1,4-dihydro-6-fluoro-4-oxo-1,8-naphthyridine-3-carboxylic acid (Cpd #4);

7-(3-methyl-1-piperazinyl)-1-(bicyclo[1.1.1]pent-1yl)-1,4-dihydro-6-fluoro-4-oxo-1,8-naphthyridine-3-carboxylic acid;

7-(4-methyl-1-piperazinyl)-1-(bicyclo[1.1.1]pent-1-yl)-1,4-dihydro-6,8-difluoro-4-oxo-3-quinolinecarboxylic acid (Cpd #99);

7-(1S, 4S-2,5-diazabicyclo[2.2.1]heptan-2-yl)-1-(bicyclo[1.1.1]pent-1-yl)-1,4-dihydro-6-fluoro-4-oxo-1,8-naphthyridine-3-carboxylic acid;

7-(2,5-diazabicyclo[2.2.2]octan-2-yl)-1-(bicyclo[1.1.1]pent-1-yl)-1,4-dihydro-6-fluoro-4-oxo-1,8-naphthyridine-3-carboxylic acid;

7-(4-(cyclopenten-3-yl)-1-piperazinyl)-1-(bicyclo[1.1.1]pent-1-yl)-1.4-dihydro-6-fluoro-4-oxo-1,8-naphthyridine-3-carboxylic acid;

7-(3-(ethylamino)methyl-1-pyrrolidinyl)-1-(bicyclo[1.1.1]pent-1-yl)-1,4-dihydro-6-fluoro-4-oxo-1,8-naphthyridine-3carboxylic acid;

7-(3-methyl-1-piperazinyl)-1-(bicyclo[1.1.1]pent-1-yl)-1,4-dihydro-6-fluoro-4-oxo-1,8-naphthyridine-3-carboxylic acid;

7-(3,4-dimethyl-1-piperazinyl)-1-(bicyclo[1.1.1]pent-1-yl)-1,4-dihydro-6-fluoro-4-oxo-1,8-naphthyridine-3-carboxylic acid;

7-(3-phenyl-1-piperazinyl)-1-(bicyclo[1.1.1]pent-1-yl)-1,4-dihydro-6-fluoro-4-oxo-1,8-naphthyridine-3-carboxylic acid, methanesulfonate;

7-(1R, 4R-2,5-diazabicyclo[2.2.1]heptan-2-yl)-1-(bicyclo[1.1.1]pent-1-yl)-1,4-dihydro-6-fluoro-4-oxo-1,8-naphthyridine-3-carboxylic acid;

7-(8-methyl-3,8-diazabicyclo[3.2.1]octan-3-yl)-1-(bicyclo[1.1.1]pent-1-yl)-1,4-dihydro-6-fluoro-4-oxo-1,8-naphthyridine-3-carboxylic acid, methanesulfonate salt;

7-(3,8-diazabicyclo[3.2.1]octan-3-yl)-1-(bicyclo[1.1.1]pent-1-yl)-1,4-dihydro-6-fluoro-4-oxo-1,8-naphthyridine-3-carboxylic acid, methanesulfonate;

7-(2-aminomethyl-morpholin-4-yl)-1-(bicyclo[1.1.1]pent-1-yl)-1,4-dihydro-6-fluoro-4-oxo-1,8-naphthyridine-3-carboxylic acid;

7-((S)-3-amino-1-pyrrolidinyl)-1-(bicyclo[1.1.1]pent-1-yl)-1,4-dihydro-6-fluoro-4-oxo-1,8-naphthyridine-3-carboxylic acid;

7-(3-amino-4-methyl-pyrrolidin-1-yl)-1-(bicyclo[1.1.1]pent-1-yl)-1,4-dihydro-6-fluoro-4-oxo-1,8-naphthyridine-3-carboxylic acid;

7-(trans-3-amino-4-methyl-pyrrolidin-1-yl)-1-(bicyclo[1.1.1]pent-1-yl)-1,4-dihydro-6-fluoro-4-oxo-1,8-naphthyridine-3-carboxylic acid;

7-(cis-3-amino-4-methyl-pyrrolidin-1-yl)-1-(bicyclo)[1.1.1]pent-1-yl)-1,4-dihydro-6-fluoro-4-oxo-1,8-naphthyridine-3-carboxylic acid; and preferably 7-(3-amino-1-pyrrolidinyl)-1-(bicyclo[1.1.1]pent-1-yl)-1,4-dihydro-6-fluoro-4-oxo-1,8-naphthyridine-3-carboxylic acid (Cpd #36); and 7-(3-amino-1-pyrrolidinyl)-1-(bicyclo[1.1.1]pent-1-yl)-1,4-dihydro-6,8-difluoro-4-oxo-3-quinolinecarboxylic acid (Cpd #84); and more preferably 7-(3-amino-1-pyrrolidinyl)-1-(bicyclo[1.1.1]pent-1yl)-1,4-dihydro-6-fluoro-4-oxo-1,8-naphthyridine-3-carboxylic acid (Cpd #36).

The compounds of Formula IB according to this invention may be provided as pharmaceutically acceptable acid addition and base salts wherein the anion or cation, respectively, does not contribute significantly to the toxicity of the salt and which salts are compatible with the standard and conventional pharmaceutically acceptable carriers and other conventional adjuvants and excipients customarily employed in producing pharmaceutical compositions adapted for oral or parenteral administration. The acid addition salts are formed by conventional techniques involving reaction of compounds of Formula I with mineral acids such as, for example, hydrochloric acid, hydrobromic acid, phosphoric acid, and sulfuric acid, and with organic carboxylic and sulfonic acids such as, for example, aspartic acid, glutamic acid, galacturonic acid, gluconic acid, acetic acid, citric acid, maleic acid, succinic acid, benzoic acid, tartaric acid, ascorbic acid, methanesulfonic acid, ethanesulfonic acid, 2-hydroxyethanesulfonic acid, p-toluenesulfonic acid, and the like.

The compounds of Formula IB with $R_3$=H or F are readily prepared as depicted in Schemes 13 and 14. For example, reaction of an appropriate 1-amino-bicyclo[1.1.1]pentane hydrochloride with an appropriate nicotinyl-(X=N) or benzoyl- (X=CH, CF, CCl, CBr, CCH$_3$) acetate 3 in a suitable solvent such as methylene chloride and in the presence of a suitable base such as diisopropylethylamine affords the novel enamino keto esters 4. The preparation of the requisite nicotinyl- and benzoyl-acetates 3 is described, for example, by D. T. W. Chu, et al., in J. Med. Chem. 28:1558–1564 (1985); J. Med. Chem. 29:2363–2369 (1986); and J. Med. Chem. 30:504–509 (1987). The enamino keto esters 4 are then cyclized to the corresponding novel naphthyridine- or quinoline-esters 5 in an suitable aprotic solvent such as tetrahydrofuran and in the presence of a suitable base such as sodium hydride. Naphthyridine- or quinoline-esters 5 can be converted to the targeted antibacterial agents of Formula I by two different routes. In the first of these, esters 5 are treated with an appropriate heterocyclic amine in a suitable solvent such as acetonitrile in the presence of a suitable base such as diisopropylethylamine or DBU (1,8-diazabicyclo[5.4.0]undic-7-ene) to provide the penultimate naphthyridine- or quinoline-esters 6. Esters 6 can be converted to the corresponding acids of Formula I ($R_5$=H,F) by treating them, for example, with aqueous sodium hydroxide. Alternatively, a second route to compounds of Formula I involves the saponification of esters 5 with, for example, aqueous sodium hydroxide, to provide the penultimate naphthyridine- or quinoline-carboxylic acids 7. The compounds 7 are the reacted with an appropriate heterocyclic amine in a suitable solvent such as pyridine, which acts as its own base, or in an aprotic solvent such as DMSO (dimethylsulfoxide) in the presence of a suitable added base such as diisopropylethylamine, to afford the targeted naphthyridine- or quinolinecarboxylic acids of Formula I ($R_3$=H,F).

A number of synthetic routes are available to prepare compounds of Formula IB with $R_3$=$NH_2$. Representative procedures utilized to prepare similar 5-aminoquinolinecarboxylic acids are described by J. M. Domagala, et al., in J. Med. Chem. 31:506–509 (1988); and in EP 0,221,463. For example, quinolone esters 5 ($R_5$=F) can be reacted with an appropriate protected amine such as benzylamine in a suitable solvent such as acetonitrile and in the presence of a suitable base such as potassium carbonate to provide quinoline esters 5 ($R_5$=$NHCH_2Ph$). Catalytic hydrogenolysis in a suitable solvent system such as acetic acid/ethanol and in the presence of a suitable catalyst such as palladium black, then affords the corresponding quinoline esters 5 ($R_3$=$NH_2$). Application of the synthetic protocols described above for Schemes 13 and 14 the provides the targeted naphthyridine- and quinoline-carboxylic acids of Formula I ($R_5$=$NH_2$).

Formula IC

The present invention also provides new naphthyridine- and quinoline-carboxylic acids of Formula I (see GENERAL FORMULA sheet). In Formula IC, X is N, CH, CF, CCl, CBr, or $CCH_3$ and $R_3$ is H, F or $NH_2$. The $R_{23}$ groups are independently hydrogen, methyl, a methyl substituted with one or more halogens (fluorine, chlorine, bromine or iodide, preferably, fluoride) such as, for example, —$CH_2F$ or are joined to form a cyclopropyl. $R_{24}$ is hydrogen, fluorine, chlorine, bromine, $C_1$-$C_6$ alkyl, or phenyl. $R_7$ is as defined above for Formula I or selected from various piperazinyl and pyrrolidinyl structures as depicted in Formula J', K', L', M', N', O', P', Q' and R' (see GENERAL FORMULA sheet) wherein $R_{26}$ is independently selected from hydrogen, $C_1$-$C_6$ alkyl optionally substituted with one or more hydroxy, fluoro, chloro, amino, $C_1$-$C_4$ alkylamino, frifluoroacetylamino and phenyl groups and $R_{27}$ is hydrogen, hydroxyl or a $C_1$-$C_6$ alkyl optionally substituted with one or more hydroxy, or halogens (fluorine, chlorine, bromine or iodide, preferably, fluoride). Typically in Formula IC, $R_7$ can be 1-piperazinyl (Formula J'), 4-methyl-1-piperazinyl (Formula K'), 3-methyl-1-piperazinyl (Formula L'), 3,5-dimethyl-1-piperazinyl (Formula M'), 2,5-diazabicyclo [2.2.1]hept-2-yl (Formula N'), 3-hydroxy-1-pyrrolidinyl (Formula O' where $R_6$ is hydrogen), 3-amino-1-pyrrolidinyl (Formula P' where $R_6$ is hydrogen), 3-amino-4-methyl-1-pyrrolidinyl (Formula Q'), 4-aminomethyl-3-hydroxy-1-pyrrolidinyl (Formula R' where $R_{26}$ is hydrogen and $R_{27}$ is hydroxyl) and 3-(ethylamino)methyl-1-pyrrolidinyl (Formula R' where $R_{26}$ is ethyl and $R_{27}$ is hydrogen).

Examples of "$C_1$-$C_6$ alkyl" are one to six carbon atoms such as methyl, ethyl, propyl, butyl, etc. and isomeric forms thereof.

Examples of Formula IC compounds of this invention include: (+,−)-6,8-difluoro-1,4-dihydro-1-(1,1-dimethyl-2-propynyl)-4-oxo-7-(1-piperazinyl)-3-quinolinecarboxylic acid methanesulfonate; (+,−)-6,8-difluoro-1,4-dihydro-4-oxo-7-(1-piperazinyl)-1-(2-propynyl)-3-quinolinecarboxylic acid methanesulfonate; (+,−)-7-(3-amino-1-pyrrolidinyl)-1,4-dihydro-1-(1,1-dimethyl-2-propynyl)-6-fluoro-4-oxo-1,8-naphthyridine-3-carboxylic acid methanesulfonate; (+,−)-7-(amino-1-pyrrolidinyl)-6,8-difluoro-1,4-dihydro-1-(1,1-dimethyl-2-propynyl)-4-oxo-3-quinolinecarboxylic acid; or (+,−)-7-(amino-1-pyrrolidinyl)-6,8-difluoro-1,4-dihydro-4-oxo-1-(2-propynyl)-3-quinolinecarboxylic acid.

The compounds of Formula I according to this invention may be provided as pharmaceutically acceptable acid addition and base salts wherein the anion or cation, respectively, does not contribute significantly to the toxicity of the salt and which salts are compatible with the standard and conventional pharmaceutically acceptable carriers and other conventional adjuvants and excipients customarily employed in producing pharmaceutical compositions adapted for oral or parenteral administration. The acid addition salts are formed by conventional techniques involving reaction of compounds of Formula I with mineral acids such as, for example, hydrochloric acid, hydrobromic acid, phosphoric acid, and sulfuric acid, and with organic carboxylic and sulfonic acids such as, for example, aspartic acid, glutamic acid, galacturonic acid, gluconic acid, acetic acid, citric acid, maleic acid, succinic acid, benzoic acid, tartaric acid, ascorbic acid, methanesulfonic acid, ethanesulfonic acid, 2-hydroxyethanesulfonic acid, p-toluenesulfonic acid, and the like.

In one method, the compounds of Formula IC can be prepared according to the general reaction Scheme 16, below. In this scheme the first step involves the coupling of a propargyl moiety with a vinyl ether 1 to form compound 2, followed by base induced cyclization to produce the quinolone 3. When the quinolone 3 is reacted with heterocycles such as piperidine or trifluoroacetamidopyrrolidine, under the normal conditions (heating at reflux temperature in acetonitrile overnight) it produces the N-1 dealkylated compound 4 with a heterocycle substituted at C-7. In a preferred synthesis, the coupling reaction of heterocycle was achieved in dimethylsulfoxide solvent in the presence of potassium dibasic phosphate buffer. Compound 4 is then hydrolyzed to the final product 5 by running the reaction at room temperature.

In another aspect, as is mentioned above, this invention is a pharmaceutical composition comprising an antibacterially effective amount of a compound of Formula IC above.

In still another aspect, this invention is a method of combatting bacterial infection in warm-blooded animals comprising administering to said animals an antibacterially effective amount of a compound of Formula IC or of a pharmaceutical composition thereof.

Pharmaceutically acceptable base salts are formed by conventional techniques involving reaction of the compounds of Formula IC with alkali (Na,K) and alkaline earth (Ca, Ba, Zn, Mn) metal bases, more preferably with alkali metal bases such as, for example, dilute solutions of sodium hydroxide and potassium carbonate. Also, pharmaceutically acceptable base salts are formed by conventional techniques involving reaction with amines such as, for example, triethylamine, dibenzylamine, triethanolamine, ethanolamine, N,N'-dibenzylethylenediamine, procaine and equivalent amines.

The antibacterial activity of the compounds of Formula IC was determined by using standard testing procedures such as the determination of minimum inhibitory concentration (MIC) by agar dilution as described in "Methods for Dilution Antimicrobial Susceptibility Tests for Bacteria That Grow Aerobically" (MFT) published January 1983 by the National Committee for Clinical Laboratory Standards, 771 East Lancaster Avenue, Villanova, Pa. 19084, USA. Briefly, MIC values are determined in unsupplemented Mueller Hinton Agar (MHA). The compounds tested are diluted serially into molten MHA at 47° C. The agar is poured into petri dishes and allowed to harden. The various bacteria used for testing are grown overnight on MHA at 35° C. and transferred to Trypticase soy broth (TSB) until a turbidity of 0.5 McFarland standard is obtained. The bacteria are diluted one to 20 in TSB and inoculated on the plates (1 µl using a Steers replicator). The plates are incubated at 35° for 20 hours and the MIC is read to be the lowest concentration of drug that completely inhibits visible growth of the bacteria.

Ciprofloxacin was used as a control and the results of the compounds of the subject invention are shown in Table CI where A is (+,−)-6,8-difluoro-1,4-dihydro-1-(1,1-dimethyl-2-propynyl)-4-oxo-7-(1-piperazinyl)-3-quinolinecarboxylic acid methanesulfonate, B is (+,−)-7-(amino-1-pyrrolidinyl)-6,8-difluoro-1,4-dihydro-1-(1,1-dimethyl-2-propynyl)-4-oxo-3-quinolinecarboxylic acid, C is (+,−)-6,8-difluoro-1,4-dihydro-4-oxo-7-(1-piperazinyl)-1-(2-propynyl)-3-quinolinecarboxylic acid methanesulfonate, D is (+,−)-7-amino-1-pyrrolidinyl)-6,8-difluoro-1,4-dihydro-4-oxo-1-(2-propynyl)-3-quinolinecarboxylic acid, and E is (+,−)-7-(3-amino-1-pyrrolidinyl)-1,4-dihydro-1-(1,1-dimethyl-2-propynyl)-6-fluoro-4-oxo-1,8-naphthyridine-3-carboxylic acid methanesulfonate.

It is to be understood that the formulas herein representing the various compounds according to the invention are intended to embrace all optical isomers, as well as racemic mixtures thereof, within the scope of the given formulas unless otherwise indicated.

In another aspect, as is mentioned above, this invention is a pharmaceutical composition comprising an antibacterially effective amount of a compound of Formula I above.

In still another aspect, this invention is a method of combatting bacterial infection in warm-blooded animals comprising administering to said animals an antibacterially effective amount of a compound of Formula I or of a pharmaceutical composition thereof.

Pharmaceutically acceptable base salts are formed by conventional techniques involving reaction of the compounds of Formula I with alkali (Na,K) and alkaline earth (Ca, Ba, Zn, Mn) metal bases, more preferably with alkali metal bases such as, for example, dilute solutions of sodium hydroxide and potassium carbonate. Also, pharmaceutically acceptable base salts are formed by conventional techniques involving reaction with amines such as, for example, triethylamine, dibenzylamine, triethanolamine, ethanolamine, N,N'-dibenzylethylenediamine, procaine and equivalent amines.

The pharmaceutical compositions of this invention may be prepared by combining the compounds of Formula I of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents stabilizers and thickening agents.

Preferably, the pharmaceutical composition is provided employing conventional techniques in unit dosage form containing appropriate amounts of the active component, that is, the compound of Formula I according to this invention.

The quantity of active component, that is the compound of Formula I according to this invention, in the pharmaceutical composition and unit dosage form thereof may be varied or adjusted widely depending upon the particular application, the potency of the particular compound, the desired concentration. Generally, the quantity of active component will range between 0.5% to 90% by weight of the composition.

The compounds according to the invention have a potent and broad antimicrobial efficacy. These properties make it possible to use them as chemotherapeutic active compounds in medicine and as substances for preserving inorganic and organic materials, in particular organic materials of all types, for example polymers, lubricants, dyes, fibers leather, paper and wood, foodstuffs and water.

The compounds according to the invention are active against Gram-negative and Gram-positive bacteria and bacterioid microorganisms. Thus, diseases caused by these pathogens can be treated.

The compounds according to the invention are particularly active against bacteria and bacterioid microorganisms. Thus, they are particularly well suited for the chemotherapy of local and systemic infections caused by these pathogens in medicine.

For example, local and/or systemic diseases caused by the following pathogens or by mixtures of the following pathogens can be treated and/or prevented: Micrococcaceae, such as staphylococci, for example Staphylococcus aureua, Staph, Epidermidis, (Staph.=-Staphylococcus); Lactobacteriaceas, such as streptococci, for example Streptococcus pyogenes, α- and β-haemolytic streptococci, non (γ-) haemolytic streptococci, enterococci and Diplococcus pneumonias (pneumococci) (Str.=Streptococcus); Enterobacteriaceas, such as encherichiae bacteria of the coli group; encherichia bacteria, for example Escherichia coil, enterobacter bacteria, for example aerogenes, E. cloacae, Klebsiella bacteria, for example K. pneumoniae, serratin, for example Serratia marcescens (E.=Enterobacter) (K.=Klebsiella), proteae bacteria of the proteus groups; proteus, for example *Proteus vulgaris, Pr. morganii, Pr. rettgeri* and *Pr. mirabilis* (Pr.=Proteus); pseudomonadaceae, such as pseudomonas bacteria, for example *Pseudomonas aeruginosa* (PS.=Pseudomonas); bacteroidaceae, such as bacteroides bacteria, for example *Bacteroides fragilis* (B.=bacteroides); mycoplasma, for example *Mycoplasma pneumonia.*

The present invention includes pharmaceutical preparations which in addition to non-toxic, inert pharmaceutically suitable excipients contain one or more compounds according to the invention or which consist of one or more active compounds according to the invention, and processes for the production of these preparations.

The present invention also includes pharmaceutical preparations in dosage units. This means that the preparations are in the form of individual parts, for example tablets, dragees, capsules, pills, suppositories and ampoules, of which the content of active substance corresponds to a fraction or a multiple of an individual dose. An individual dose preferably contains the amount of active compound which is given in one administration and which usually corresponds to a whole, a half or a third or a quarter of a daily does.

By non-toxic, inert pharmaceutically suitable excipients there are solid, semi-solid or liquid diluents, fillers and formulation auxiliaries of all kinds. Preferred pharmaceutical preparations are tablets, dragees, capsules, pills, granules, suppositories, solutions, suspensions and emulsion, pastes, ointments, gels, creams, lotions, powders and sprays.

Tablets, dragees, capsules, pills and granules can contain the active compound or compounds alongside the customary excipients such as (a) fillers and extenders, for example starches, lactose, sucrose, glucose, mannitol and silica, (b) binders, for example carboxymethylcellulose, alginates, gelatine and polyvinylpyrrolidone, (c) humectants, for examples glycerine, (d) disintegrating agents, for example agar-agar, calcium carbonate and sodium carbonate, (e) solution retarders, for example paraffin, and (f) absorption accelerators, for example quaternary ammonium compound (g) wetting agents, for example cetyl alcohol or glycerine monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the above mentioned excipients, can also be in a microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid) or mixtures of these substances.

Ointments, pastes, creams and gels can contain the customary excipients in addition to the active compound or compounds, for example animal and vegetable fats, waxes, paraffins, starch, tragacanth, cellulose derivatives, polyethylene glycols, silicones, bentonites, silica, talc and zinc oxide or mixtures of these substances.

Powders and sprays can contain the customary excipients in addition to the active compound or compounds, for example lactose, talc, silica, aluminum hydroxide, calcium silicate and polyamide powders or mixtures of these substances. Sprays can additionally contain the customary propellants, for example chlorofluorohydrocarbons.

Solutions and emulsions can contain the customary excipients in addition to the active compound or compounds, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerine-formal, tetrahydrofurfuryl alcohol, polyethylene glycols and fatty acid esters of sorbitan, or mixtures of these substances.

For parenteral administration, the solutions and emulsions can be in a sterile form which is isotonic with blood.

Suspensions can contain the customary excipients in addition to the active compound or compounds, such as liquid diluents, for example water, ethyl alcohol or propylene glycol, suspending agents, for example ethoxylated isostearyl alcohols, polyoxyethylene sorbitol esters and sorbitan esters, microcrystalline cellulose, aluminum metahydroxide, betonite, agar-agar and tragacanth or mixtures of these substances.

The formulation forms mentioned can also contain dyestuffs, preservatives and additives which improve the odour and flavour, for example peppermint oil and eucalyptus oil, and sweeteners, for example saccharin.

The therapeutically active compounds should preferably be present in the above mentioned pharmaceutical preparations in a concentration of about 0.1 to 99.5, preferably of about 0.5 to 95, percent by weight of the total mixture.

The above mentioned pharmaceutical preparations can also contain other pharmaceutical active compounds in addition to the active compounds according to the invention.

The above mentioned pharmaceutical preparations are manufactured in the usual manner according to known methods, such as by mixing the active compound or compounds with the excipient or excipients.

The active compounds or the pharmaceutical preparations can be administered locally, orally, parenterally, intraperitoneally and/or rectally, preferably orally or parenterally, such as intravenously or intramuscularly.

In general, it has proved advantageous in medicine to administer the active compound or compounds in total amounts of about 0.5 to about 50, preferably 1 to 30, especially preferably 1–20 mg/kg of body weight, orally or parenterally, every 24 hours, optionally in the form of several individual administrations, in order to achieve the desired results. An individual administration contains the active compound or the active compounds preferably in amounts of about 1 to about 250, especially of 3 to 60, mg/kg of body weight. However, it can be necessary to deviate from the dosages mentioned and in particular to do so as a function of the nature and body weight of the subject to be treated, the nature and the severity of the illness, the nature of the preparation and of the administration of the medicine, and the time or interval over which the administration takes place. Thus it can suffice in some cases to manage with less than the above mentioned amount of active compound whilst in other cases the above mentioned amount of active compound must be exceeded. The particular required optimum dosage and the type of administration of the active compounds can easily be decided by anyone skilled in the art, on the basis of his expert knowledge.

The new compounds can be utilized as feedstuff.

EXAMPLE 1

Preparation of 2-[4-(1-Cyclopropyl-3-carboxy-6,8-difluoro-1,4-dihydro-4-oxo-7-quinolinyl)-1-piperazinyl]2-butenedioic acid, dimethyl ester The preparation of this compound is illustrated in Scheme 3, below. The starting material "A" is disclosed in J. Med. Chem., 31(5), 991-1001, by Domagala, et al. This ester (1.64 g, 5.27 mmol) dissolved in 120 ml of DMF and 590 mg, (6.84 mmol) of piperazine was added with stirring overnight at 55° C. The mixture was allowed to cool to 23° C., filtered and washed with ethyl alcohol to yield 594 1 mg of a white powder "B".

The amino ester B (500 mg, 1.32 mmol) was dissolved in 20 ml of chloroform and 163 μL (1.32 mmol of dimethyl acetylene dicarboxylate was added. The product C was then obtained by evaporating off the solvent.

Product C (250 mg, 0.48 mmol) was dissolved in 2.0 ml of THR and 1.0 ml (2.0 mmol) of potassium hydroxide and stirred at 23° C. for 24 hours. The THF was then removed by vacuum and the residue dissolved in 25 ml of water and washed with 25 ml of ethyl acetate. The acidity was adjusted to pH 6 and a white participate formed. The participate D was filtered, air dried and washed with ethyl alcohol to yield 180 mg of the subject product in 81% yield.

EXAMPLE 2

Preparation of 2-[4-(1-Ethyl-3-carboxy-6-fluoro-1,4-dihydro-4-oxo-7-quinolinyl)-1-piperizinyl]2-butanedioic acid, dimethyl ester.

The preparation of this compound is illustrated in Scheme 4, below. The starting material A is disclosed in J. Chem. Soc., 1664 (1967) by Bartett, R. K. and Humphrey, L. R.

The starting material A (1 g, 37 mmol) was admixed with 14 ml of pyridine and 1.58 g (18.5 mmol) of piperazine at 60° C. for about 4 hours. The solvent was removed under nitrogen and the product B recrystallized from ethyl alcohol. The piperazine product B yield was 72%, 0.85 g, melting point 195°-201° C.

Product B (0.4 g, 1.25 mmol) was admixed with 10 ml. of DMF and 154 λ (1.25 mmol) of acetylene dicarboxylate at room temperature for about 2 hours. The solvent was then evaporated under nitrogen and the residue recrystallized from DMF and ethyl alcohol. The product C was dried in an oven at 60° C. to obtain 265 mg, 235°-239° C. melting point, in 46% yield.

EXAMPLE 3

Preparation of 2-[4-(1-Cyclopropyl-3-carboxy-6-fluoro-1,4-dihydro-4-oxo-7-quinolinyl)-1-piperazinyl]2-butenedioic acid, dimethyl ester The preparation of this compound is illustrated in Scheme 5, below. The starting material A is disclose din Chemical Abstracts 106:201748f.

The starting material A (500 mg, 1.45 mmol) was dissolved in 10 ml chloroform and added to 178 μL (1.45 mmol) dimethylacetylene dicarboxylate. The mixture was stirred overnight at room temperature and then chromatographed over 150 g of silica dioxide and flushed with chloroform and ethyl alcohol (96:4). The product B was recrystallized in ethyl acetate to yield 727 mg of white solid.

The ester product B (200 mg, 0.41 mmol) was added to 1 ml of THF, 2 ml of 2N potassium hydroxide and stirred at 30° C. for about 4 hours. After all material had dissolved the THF was evaporated and the remaining mixture was diluted with 10 ml of water. The pH was adjusted to 7 and a white participate formed. The participate was filtered and dried to yield 141 mg of a white solid product C, melting point 225°-226° C. 73% yield.

EXAMPLE 4

Preparation of 2-[4-(3-carboxy-1-cyclopropyl-6,8-difluoro-1,4-dihydro-4-oxo-4-oxo-7-quinolinyl)-1-piperazineyl]-2-pentenedioic acid-(E)-1,5-dimethyl ester The preparation of this compound is illustrated in Scheme 6, below. The amino acid (A, 350 mg, 1.0 mmol) was dissolved in DMF (6.0 mL) and 3-chloro-1,5-pentenedioic acid dimethyl ester (193 mg, 1.0 mmol) was added. The reaction was stirred overnight at 50° C., then DBU (2 equivalents) was added. The reaction immediately turned red. The reaction was stirred for 1 hour, then the solvent was removed under a stream of dry $N_2$ gas. The residue was chromatographed (flash $SiO_2$, 100 g), eluting with methylene chloride/methanol/acetic acid (90:10:0.5), to give the product as a pale orange solid (167 mg, 33%). MP=158°-61° C., dec.

EXAMPLE 5

Preparation of 2-[4-(5-amino-3-carboxy-1-cyclopropyl-6,8-difluoro-1,4-dihydro-4-oxo-7-quinolinyl)-1-piperazinyl]-2-butenedioic acid, (E)-1,4-dimethyl ester The preparation of this compound is illustrated in Scheme 7, below. The starting material A is disclosed in J. Med. Chem., 30, p. 2285 (1987) by L. Mitscher, et al.

The starting material A (27.46 g, 97.4 mmol) was admixed with 41 ml of acetic anhydride and 17.4 g (117.4 mmol) triethylorthoformate and refluxed for about 3 hours. The mixture was evaporated at 60° C. and azeotroped with toluene three times to yield 32.98 g of product B.

The enol ether B (12 g, 35.5 mmol) was added to 2.05 g, 36 mmol of cyclopropylamine in 50 ml of ethylene chloride and stirred at room temperature. This mixture was evaporated under vacuum and the product added to 600 g silica gel packed and eluted with methylene chloride. Approximately 11.43 g of the product C was obtained in a 92% yield and had a melting point of 88°-92° C.

The enamine C (10 g, 27 mmol) was stirred in 185 ml of THF at 0° C. and 1.14 g of a 60% oil dispersion of sodium hydride was added. The mixture was evaporated under vacuum, transferred to a separation funnel, extracted three times with chloroform and dried over magnesium sulfate. This procedure yielded 10.6 g of product which was recrystallized from ethyl acetate to give 8.28 g of product D, melting point 166°-169° C., in 88% yield.

The tetrafluoro ester D (6.0 g, 18.7 mmol) was admixed to 2.75 g potassium carbonate and 2.0 g (18.7 mmol) of benzylamine in 200 ml acetonitrile and refluxed for 3 hours. The solid was filtered off, the filtrate evaporated and the residue added to 700 g of silica gel packed and eluted with 3% methanol/methylene chloride. This procedure afforded 4.15 g of E in 55% yield, melting point 130°-133° C.

The benzylamine E (1.85 g, 4.45 mmol) was dissolved in 17 ml ethanol and 11 ml acetic acid with 10% palladium on carbon (0.28 g) and shaked for 1.5 hours under 12 pounds hydrogen pressure. The mixture was filtered rinsing with chloroform. The filtrate was evaporated and the residue triturated with ethanol to give 1.23 g of the product F in 85% yield, melting point 228°-232° C.

A mixture of trifluoro ester F (0.5 g, 1.53 mmol) and 0.65 g of piperazine (7.65 mmol) in 25 ml of acetonitrile was refluxed for 1 day. The mixture was evaporated under vacuum and the residue added to 50 g of silica gel packed with 5% methanol/methylene chloride. Elution with 5-15% methanol/methylene chloride afforded 0.54 g (90% yield) of product which was recrystallized from ethyl acetate/methylene chloride, melting point 209°-219° C.

Ester G (0.24 g, 0.62 mmol) was stirred for 1 day in a 6 ml of tetrahydrofuran and 3 ml of 2N aqueous potassium hydroxide. The tetrahydrofuran was evaporated off under vacuum and the resulting aqueous layer was neutralized with 2N hydrochloric acid. The product was filtered off and washed with water, ethanol, and ether to afford 0.11 g (49% yield) of product H, melting point 228°-235° C.

Product I was prepared as B in example 2. The amino acid H (0.17 g) was converted to 64 mg (27% yield) of I after silica gel chromatography (0.5% acetic acid, 10% methanol/methylene chloride) and recrystallization from methanol/methylene chloride, mp (171°-186° C.

EXAMPLE 6

Preparation of
2-[4-(3-carboxy-1-cyclobutyl-6,8-difluuoro-1,4-dihydro-4-oxo-7-quinolinyl)-1-piperazinyl]-2-butenedioic acid (E)-1,4-dimethyl ester The preparation of this compound is illustrated in Scheme 8, below. The starting material A is disclosed in J. Med. Chem. 31, p. 991 (1988) by J. M. Domagala et al.

Piperazine was added to A as in Example 5. Refluxing A (2.0 g) with piperazine in acetonitrile for 2 days followed by column chromatography afforded 2.03 g (84% yield) of B which was recrystallized from EtOAc/CH$_2$Cl$_2$ (mp 188°-192° C.).

Ester B (0.5 g) was refluxed in 36 ml of 6N hydrochloric acid for 7 hours. Evaporation of the solvent under nitrogen and recrystallization of the residue from ethanol afforded 0.296 g (64%) of product C, mp 310°-328° C.

Product D was prepared as B in example 2. The amino acid C (0.27 g) was converted to 0.214 g (57% yield) of D after recrystallization from ethanol (mp 215°-221° C.).

EXAMPLE 7

Preparation of
2-[4-(3-carboxy-1-benzene-4-fluoro)-6,8-difluoro-1,4-dihydro-4-oxo-7-quinolinyl)-1piperazinyl]-2-butenedioic acid, (E)-1,4-dimethyl ester The preparation of this compound is illustrated in Scheme 9, below. The starting material A is disclosed in J. Med. Chem. 30, p. 504 (1987) by D. T. W. Chu et al.

Product B was prepared as B in example 2. The amino acid A (0.4 g) was converted to 0.35 g (64% yield) of B after recrystallization from dimethyl formamide/ethanol (mp 244°-251° C.).

EXAMPLE 8

Preparation of
2-[4-(3-carboxy-1-benzene(2,4-difluoro)-1,4-dihydro-4-oxo-7-quinolinyl)-1-(3-aminopyrrolidinyl)]-2-butenedioic acid, (E)-1,4-dimethyl ester The preparation of this compound is illustrated in Scheme 10, below .The starting material A is disclosed in J. Med. Chem. 30, p. 504 (1987) by D. T. W. Chu et al.

Product B was prepared as B in example 2. The amino acid A (0.23 g) was converted to 85 mg (27% yield) of B after chromatography over 80 g silanized silica gel packed and eluted with chloroform and recrystallization from methylene chloride/hexane (mp 176°-182° C.).

EXAMPLE 9

Preparation of
2-[4-(3-carboxy-1-cyclopropyl-6,8-difluoro-1,4-dihydro-4-oxo-7-quinolinyl)-1-(3-aminopyrrolidinyl)]-3-butenoic acid -(E)-1-methyl ester The preparation of this compound is illustrated in Scheme 11. The preparation of the starting material A is described as "B" in example 10, scheme 2.

The amino acid A (200 mg, 0.57 mmol) was dissolved in DMF (1.0 mL) and heated to 150° C. for 4 h with methylacetonacetate (108 uL, 1.0 mmol). The mixture was then cooled and DMF removed under a stream of dry nitrogen. The residue was extracted with methylene chloride and concentrated, then chromatographed over silanized silica gel, eluting with 3% ethanol in methylene chloride, giving the product B (159 mg, 63%) as a pale yellow powder. MP—189°-91° C., dec.

EXAMPLE 10

Preparation of
2-[4-(3-carboxy-1-cyclopropyl-6,8-difluoro-1,4-dihydro-4-oxo-7-quinolinyl)-1-(3-aminopyrrolidinyl)]-2-butenedioic acid-(E)-1,4-dimethyl ester The preparation of this compound is illustrated in Scheme 2. The trifluoro ester (described as A in Scheme 3, 18.0 g, 57.8 mmol) was admixed with 3-acetamidopyrrolidine (7.41 g, 57.8 mmol) in acetonitrile (100 mL). Triethyl amine (8.22 mL, 59 mmol) was added and the mixture stirred at 57° C. for 24 h. The solvent was removed and the residue dissolved in methylene chloride and washed with water, then concentrated and chromatographed over flash silica gel eluting with 5% ethanol in methylene chloride to give the product A (15.4 g, 64%) as a white solid. MP=132°-5° C.

The product A (2.0 g, 4.8 mmol) was then dissolved in 2N KOH (14 mL) and heated to reflux for 6 h, then neutralized under heating with acetic acid. On cooling the mixture was filtered and the filtrate discarded. The product was then dissolved in 2.5% acetic acid in water (2.5 mL/100 mL) and filtered thru a medium frit. The filtrate was made to pH 10 with 50% sodium hydroxide and neutralized with acetic acid to give a white powder which was filtered and washed with methanol and ether to give B as a white powder (809 mg, 48%).

The product B (400 mg, 1.2 mmol) was dissolved in a mixture of chloroform (3.0 mL) and DMF (0.5 mL) and dimethylacetylenedicarboxylate (141 uL, 1.2 mmol) was added. The mixture was stirred for 24 h at 23° C., then the solvent was removed under a stream of dry nitrogen gas and the residue was chromatographed over silanized silica gel, eluting with chloroform to give the product C (354 mg, 63%) as an off white solid. MP=173°-5° C., dec.

EXAMPLE 11

Preparation of
2-[4-(1-Cyclopropyl-3-carboxy-5,6,8-trifluoro-1,4-dihydro-4-oxo-7-quinolinyl)-1-piperazinyl]2-butenedioic acid, dimethyl ester.

The preparation of this compound is illustrated in Scheme 13, below, and the starting material A is disclosed in Scheme 7.

The tetrafluoro ester A (0.44 g) was admixed with 5 ml of pyridine and 0.12 g of piperazine for about 1 day. The pyridine was then evaporated off under nitrogen and the residue chromatographed over silica gel (5-10% methanol/methylene chloride) to afford 0.166 g (31yield) of the product B which was recrystallized from methylene chloride/hexane. mp 227° C.

The product C was prepared as C in example 1. The amino ester B (0.23 g, 0.58 mmol) was converted to 0.21 g (67% yield) of C after chromatography over 20 g silica gel packed and eluted with 3% methanol/methylene chloride and recrystallization from ethanol/ethyl acetate (mp 244°-227° C.).

The ester C (0.15 g) was admixed with 5 ml of methylene chloride and 100 mg of potassium trimethylsilanolate at room temperature for about two days. Column chromatography over 20 g of silica gel packed and eluted with 0.5% acetic acid, 10% methanol in methylene chloride followed by recrystallization from ethanol afforded 60 mg (41% yield) of product D. mp 215°-223° C.

The ester D (2g, 6/08 mmol) was refluxed in 6N (150 ml) hydrochloric acid for about seven hours and evaporated at 70° C. The residue was recrystallized from ethyl alcohol to yield 0.59 g of product E, melting point 169°-177° C.

The tetrafluoro acid E (0.4 g, 1.33 mmol) was admixed with 5.5 ml of pyridine and 0.42 (4.8 mmol) of piperazine and heated to 60° C. for about 1.5 hours. The pyridine was then evaporated off under nitrogen and the product recrystallized from ethyl alcohol with ethyl acetate to yield 0.34 g of product F, melting point 230°-238° C., in 70% yield.

The piperazine compound F (0.2 g, 0.4 mmol) with 5 ml of DMF was added to 66 μL (0.54 mmol) of acetylene dicarboxylate and stirred at room temperature for about 2 hours. The solvent was removed under nitrogen, the residue recrystallized from ethylalcohol and dried in vacuum at 60° C. to yield the product F, 0.202 mg, melting point 170°-180° C., in 70% yield.

EXAMPLE 12

Preparation of
1-(bicyclo[1.1.1]pent-1-yl)-6,8-difluoro-1,4-dihydro-4-oxo-7-(1-piperazinyl)-3-quinlinecarboxylic acid (Cpd #1)

Part A

A 50 ml one-neck round bottom flash is equipped with a magnetic stirring bar condenser and gas inlet. To this flash is added ethyl 2,3,4,5-tetrafluorobenzoyl acetate (2.8 g. 10.6 mmol) along with acetic anhydride (6.5 g, 63.6 mmol) and triethyl orthoformate (2.4 g, 15.9 mmol). After stirring, within a few minutes the mixture is completely dissolved to give a clear solution. This mixture is refluxed for 3 hours (oil bath at about 140° C.). The condenser is periodically removed to allow EtOAc to evaporate as it is formed. At this time the TLC shows a new product present. The volatiles are removed under reduced pressure and the contents of the flash are further concentrated to a constant mass at high vacuum (0.4 mmHg). $^1$H nmr shows a mixture of the desired cis and trans product. 3.1 g of an orange oil is obtained which is stored under nitrogen in the freezer until needed.

Part B

1-Amino-bicyclo[1.1.1]pentane hydrochloride (250 mg, 2.09 mmol) is placed into a 50 ml round bottom flash equipped with a magnetic stirring bar and gas inlet. Then 10 ml of CH$_2$Cl$_2$ is added. Next the enol ether obtained above (670 mg, 2.09 mmol), dissolved in 2 ml of CH$_2$Cl$_2$ is added, and the mixture is cooled to 0° C. with an ice bath. Next a solution of Hunig's base (270 mg, 2.09 mmol) in 3 ml of CH$_2$ CL$_2$ is added and the mixture is allowed to stir for one hour at 0° C. The reaction mixture is allowed to stir an additional hour at room temperature. TLC of the mixture at this time shows complete consumption of starting material. The reaction mixture is concentrated to leave behind an orange waxy solid. The mixture is chromatographed on silica gel. Elution with 5:1 hexane/EtOAc gives 470 mg of the enamino keto ester as a light yellow gummy solid.

Part C

In a flame dried 35 ml flask equipped with a pressure equalizing addition funnel, magnetic stirring bar, and gas inlet is placed NaH (40 mg, 0.560 mmol) as a 50% oil suspension. Next 5 ml of dry THF is added and the whole is cooled to 0° C. with an ice bath. Next the enamino keto ester obtained above (100 mg, 0.280 mmol) dissolved in 20 ml of dry THF is added dropwise via the addition funnel. After the addition is complete the reaction mixture is heated in an oil bath at 50° C. for 15 minutes. TLC at this time shows complete consumption of starting material. The reaction mixture is cooled to 0° C. and treated with 0.5 ml of HOAc to consume any unreacted NaH. The mixture is then concentrated in vacuum to give a yellow gummy solid. After further drying at 0.4 mmHg for one hour a light yellow solid results. The crude material is chromatographed on silica gel (elution 400 ml CHCl$_3$ followed by 500 ml 5%

MeOH/CHCl₃) to give 1-(bicyclo[1.1.1]pent-1-yl-1,4-dihydro-6,7,8-trifluoro-4-oxo-3-quinoline carboxylic acid ethyl ester as a white solid (68 mg, mp-176°–178° C.)).

Part D a 25 ml flame dried round bottom flash is equipped with a reflux condenser, magnetic stirring bar, and gas inlet. The system is purged with nitrogen and the trifluoroquinolone obtained above (150 mg, 0.445 mmol) is added along with 10 ml dry CH₃CN. Then piperazine (191 mg, 2.22 mmol) is added. The resultant red solution is brought to reflux. As reflux begins the solution becomes yellow. The mixture is left to reflux overnight. The reaction mixture is concentrated and triturated with ether to leave a pale peach colored solid. This gives a 140 mg sample (mp-185°–187° C.) which is pure by ¹H nmr and 100 mg of a pink solid which has a mixture of materials. The pure material is pushed to the next step.

Part E

The ester obtained above (90 mg, 0.223 ml) is suspended in 1 ml of water and 1.2 ml 1N aqueous NaOh is added. The suspension is refluxed for one hour. The solution is cooled and adjusted to pH near 7.5 with 1N HCl. The precipitate is filtered and washed with water and dried in vacuo to give 55 mg of Compound No. 1 (mp-225°–226° C.).

EXAMPLE 13

Preparation of 1-(bicyclo[1.1.1]pent-1-yl)-6-fluoro-4-oxo-7-(1-piperazinyl)-3-quinolinecarboxylic acid (Cpd #20

Part A

A 250 ml flame dried round bottom flash is equipped with a pressure equalizing addition funnel, magnetic stirring bar, and gas inlet. The Flash is charged with a 50% sodium hydride-in-oil suspension (3.74 g, 78.0 mmol) along with 20 ml of dry THF. The slurry of NaH is cooled to 0° C. with an ice bath and a solution of 2,4-dichloro-5-fluoroacetophenone (7.8 g, 37.6 mmol) in 100 ml of diethylcarbonate (100 ml) is added slowly (dropwise) to the slurry of NaH. After the addition is complete the mixture is stirred at room temperature until gas evolution ceases (30 minutes). The deep red-orange solution is then heated to 80° C. for 1.5 hours. The reaction mixture is poured into an ice-cold water (250 ml) solution containing acetic acid (8 ml). The mixture is extracted (3 × 150 ml) with ether, dried over Na₂SO₄, and concentrated to an orange oil. The oil is distilled at high vacuum (1mmHg 133°–135° c.). 7.9 g of ethyl 2.4-dichloro-5-fluorobenzyoylacetate is obtained as a light yellow oil.

Part B

Into a 25 ml flash equipped with a magnetic stirring bar and reflux condenser is placed the benzoylacetate obtained above (2.0 g, 7.17 mmol) along with acetic anhydride (4.75 g 46.6 mmol) and triethyl orthoformate (1.6 g, 10.8 mmol). The solution is heated at 130° C. for 2.5 hours with frequency removal of the condenser to remove ethyl acetate as it forms during the reaction. The solution is concentrated under reduced pressure to constant weight.

Part C

Into a 50 ml flask equipped with a magnetic stirring bar and gas inlet is placed the enol ether obtained above (840 mg, 2.50 mmol) and 1-amino-bicyclo[1.1.1]-pentane hydrochloride (300 mg, 2.50 mmol) in 15 ml of CH₂Cl₂. This solution is cooled to 0° C. and Hunig's base (323 mg, 2.50 mmol) is added. The mixture is stirred until room temperature is reached. The reaction mixture is concentrated to a solid material. TLC shows starting material to be consumed. The mixture is chromatographed on silica gel (MPLC) eluting hexane/ethyl acetate (7:1). 720 mg of the enamino keto ester is obtained as a yellow viscous oil.

Part D

Into a 100 ml flame dried flask equipped with a pressure equalizing addition funnel, magnetic stirring bar, and gas inlet was placed NaH (169 mg 50% oil suspension, 3.52 mmol) along 10 ml of dry THF. The slurry was cooled to 020 C. and a solution of the enamino keto ester obtained above (630 mg, 1.76 mmol) dissolved in 35 ml of dry THF was added dropwise via the additional funnel. After the addition was complete the mixture was heated at 80° C. for 3 hours. The mixture was then cooled to 0° C. and acidified with 2 ml of glacial acetic acid. Concentration to dryness, followed by chromatography on silica gel (eluted with CHCl₃, moving to 5% MeOh/CHCl₃) gate 470 mg of 1-(bicyclo[1.1.1]pent-1-yl)-1.4-dihydro-6-fluoro-7-chloro-4-oxoquinoline-3-carboxylic acid ethyl ester (m.p.–223°–225° C.).

Part E

The quinolene ester obtained in the previous step (349 mg, 1.04 mmol) is slurried in 3 ml of H₂O. Next 5 ml of 1N NaOh is added and the mixture is brought to reflux. After one hour reflux, TLC shows starting material to be consumed and a low Rf material forms. The mixture is cooled to 0° C. and acidified to pH 7. The solids are filtered, washed with water, cold ethanol, and ether. Drying under vacuum gives 290 mg of an off-white solid (mp>250° C.).

Part F

The quinolone acid obtained above (120 mg, 0.390 mmol) is slurried in 3 ml of pyridine and piperazine (134 mg, 1.56 mmol) is added. The mixture is brought to reflux and stirred under nitrogen at this temperature for 18 hours. At this time water is added to give a solution which is extracted (4 × 50 ml) with chloroform. Reverse phase TLC (elution with 4:1 MeOh/0.05 M Bu₄N-HSO₄) shows UV active material of extracts different than starting material. The chloroform layer is dried and concentrated to give 116 mg of an off-white solid. Recrystallization from 5:1 Et₂O/CH₂Cl₂ gives 75 mg of Compound No. 2 (mp-233°–235° C.).

Following the general procedure of Examples 1 and 2, and making non-critical variations, except starting with the appropriate naphthyridine- or quinoline-esters 5 or the corresponding acids 7 and introducing the appropriate heterocyclic amine (R₇), the compounds described in Table I can be prepared.

The compounds according to the invention have good actions against Gram-positive and Gram-negative bacteria.

The effectiveness of the subject compounds on some bacteria were obtained by performing a dipped disk assay. The antibacterial activity of the compounds is determined by the disk-diffusion method. Paper disks (12.7 mm) were loaded with 0.10 ml of drug solution prepared at a concentration of 1 and 0.1 mcg/ml; the disks were allowed to air dry. They were then applied to the surface of microorganism-seeded agar assay trays, which contained the bacterial strain Pseudomonas aeruginosa UC 95 )PA), Escherichia coli UC 51 (EC) or Staphylococcus aureus UC 80 (SA). The assay trays were incubated overnight under aerobic condition to allow for the growth of the organisms. Zones of growth inhibition due to the action of the antibiotic were then measured to the nearest millimeter.

| | | (Growth Inhibition Zone, in mm) | | |
|---|---|---|---|---|
| Compound | Conc | EC | PA | SA |
| 1 | 1 mg/ml | 35 | 44 | 28 |
|   | 0.1 mg/ml | 30 | 35 | 25 |
| Cipro | 1 mg/ml | 33 | 48 | 28 |
| 2 | 1 mg/ml | 30 | 41 | 28 |
|   | 0.1 mg/ml | 30 | 35 | 25 |
| Cipro | 1 mg/ml | 35 | 48 | 30 |

The result show that compounds 1 and 2, corresponding to Examples 1-2, above, have potent gram negative and positive activity as compared to the commercially available antibacterial Ciprofloxacin ("Cipro"), from Miles Pharm. Div., West haven, CT.

Compounds of this invention can also be tested for in vitro antimicrobial activity using standard testing procedures such as the determination of minimum inhibitory concentration (MIC) by agar dilution as described in "Methods for Dilution Antimicrobial Susceptibility Tests for Bacteria That Grow Aerobically" (MFT) published Jan. 1983 by the National Committee for Clinical Laboratory Standards, 771 East Lancaster Avenue, Villanova, Penna. 19084, USA. Briefly, MIC values are determined in unsupplemented Mueller Hinton Agar (MHA). The compounds tested are diluted serially into molten MHA at 47° C. The agar is poured into petri dishes and allowed to harden. The various bacteria used for testing are grown overnight on MHA at 35° C. and transferred to Trypticase soy broth (TSB) until a turbidity of 0.5 McFarland standard is obtained. The bacteria are diluted one to 20 in TSB and inoculated on the plates (1µl using a Steers replicator). The plates are incubated at 35° C. for 20 hours and the MIC is read to be the lowest concentration of drug that completely inhibits visible growth of the bacteria. The MIC test results of selected of Formula B compounds of this invention are found in Tables B2-B9.

The compounds according to the invention have a potent and broad antimicrobial efficacy. These properties make it possible to use them as chemotherapeutic active compound in medicine and as substances for preserving inorganic and organic materials. In particular organic materials of all types, for example polymers, lubricants, dyes, fibres, leather, paper and wood, foodstuffs and water.

The compounds according to the invention are active against Gram-negative and Gram-positive bacteria and bacterioid microorganisms. Thus, diseases caused by these pathogens can be treated.

The compounds according to the invention are particularly active against bacteria and bacterioid microorganisms. Thus, they are particularly well suited for the chemotherapy of local and systemic infections caused by these pathogens in medicine.

For example, local and/or systemic diseases caused by the following pathogens or by mixtures of the following pathogens can be treated and/or prevented: Micrococcaceae, such as staphylococci, for example Staphylococcus aureus, Staph. Epidermidis, (Staph.=-Staphylococcus); Lactobacteriaceae, such as streptococci for example Streptococcus pyogenes, α- and β-haemolytic streptococci, no (γ-) haemolytic streptococci, enterococci and Diplococcus pneumoniae (pneumococci) (Str.=Streptococcus); Enterobacteriaceae, such as encherichiae bacteria of the coli group; encherichia bacteria, for example Escherichia coli, enterobacter bacteria, for example, E. aerogenes, E. cloacae, Klebsiella bacteria, for example K. pneumoniae, serratin, for example Serratia marcescens (E.=Enterobacter) (K.=Klebsiella), proteae bacteria of the proteus groups; proteus, for example Proteus volgaris, Pr. morganii, pr. rettgeri and Pr. mirabilis (Pr.=Proteus); pseudomonadaceae, such as pseudomonas bacteria, for example Pseudomonas aeruginosa (PS.=Pseudomonas); bacteriodaceae, such as bacteriodes bacteria, for example Bacteriodes fragilis (B.=Bacteroides); mycoplasma, for example Mycoplasma pneumonia.

EXAMPLE 14

(+,−)-7-(3-amino-1-pyrrolidinyl)-1,4-dihydro-1-(1,1-dimethyl-2-propynyl)-6-fluoro-4-oxo-1,8-naphthyridine-3-carboxylic acid methanesulfonate The preparation of this compound is structurally depicted in Scheme 17, below.

To a solution of pyridine enolether 6 (620 mg, 1.8 mM) in ethanol (5 ml) at room temperature dimethylpropargyl amine (0.6 ml, dried over $MgSO_4$) was added with stirring. The reaction mixture was concentrated in vacuo after 3.5 hours. This coupled intermediate 7 was used directly for the next cyclization step. It was dissolved in THF (10 ml) and cooled in an ice bath. NaH (100 mg of 50% NaH dispersed in oil) was added and the mixture was stirred at 0° C. for 2 hours and for 2 hours at room temperature. The desired product was precipitated out of the reaction mixture which was filtered, washed with $H_2O$ and $Et_2O$ and dried to obtain the first crop of 8 (310 mg). The filtrate was washed with EtOAc and the organic layer was taken, dried over $MgSO_4$ and concentrated in vacuo. The residue was triturated with ether to obtain the 2nd crop of 8; (55 mg). Total 365 mg (1.1 mM), yield 61%; mp 229°–231° C. (decomp.).

A heterogeneous mixture of the naphthridine ester 8 (168 mg, 0.5 mM), 3-N-trifluoroacetyl aminopyrrolidine hyderochloride salt (120 mg, 0.55 mM) and $K_2HPO_4$ (220 mg) in DMSO was stirred at room temperature for 2 days. The desired trifluoroacetylaminopyrrolidine coupled product 9 was precipitated out of the reaction mixture and the solid was filtered, washed with $H_2O$ and EtOAc and dried to obtain the pure product 9 (225 mg, 4.7 mM) in 94% yield; mp268°–270° C. (decomp.). 1H NMR (d$_6$-DMSO) δ 9.7 (s, 1H), 9.1 (s, 1H), 7.89 (d, J=13 Hz, 1H), 4.5 (broad multiplet, 1H), 4.21 (q,J=7 Hz, 2H), 3.7∼4.1 (m, 5H including one single at 3.8 for C≡C—H), 2.0∼2.3 (m, 8H including one singlet at 2.12 for 6), 1.27 (t, J=7 Hz, 3H); IR (mineral oil) 1695, 1630, 1444 cm$^{-1}$; HRMS (m/z 482.1569 (calcd for $C_{22}H_{22}F_4N_4O_4$ 482.1577).

Naphthridine ester 9 (650 mg, 1.35 mM) was dissolved in DMSO (20 ml) containing aq. NaOH (240 mg of 50% NaOH in 3 l $H_2O$ by heating briefly at 75° C.). The mixture was allowed to cool to room temperature over 1 hour and then left at room temperature overnight. The DMSO was removed in vacuo and the residue was dissolved in 15 ml of $H_2O$ whose pH was 9.8 a this point. The pH of the solution was adjusted to 7 by use of 1N HCl. The carboxylic acid product was precipitated out of the solution which was filtered, washed with $H_2O$ and dried to obtain 360 mg of solid which was found to be the acid 10 with trifluoroacetyl group of the pyrrolidine ring intact. The filtrate solution was concentrated again in vacuo and the residue was redissolved in $H_2O$ (5 ml). the pH of the solution was readjusted to 7 to induce the additional solid precipitation. The solid precipitate was filtered, washed with $H_2O$ followed by $Et_2O$ and dried to obtain 135 mg of solid.

Two batches of solid (360 mg and 135 mg) were subjected into a hydrolysis reaction condition separately. A mixture of 360 mg solid, 150 mg of 50% NaOH, 15 ml of $H_2O$ and 5 ml of methanol was heated at reflux temperature for 2 hours. The pH of the solution was adjusted to 7 by use of 1N HCl and the solid precipitate was filtered, washed with $H_2O$ and $Et_2O$. After drying 260 mg of the completely hydrolyzed product, 11 was obtained. By following the same procedure with 135 mg of the other batch of solid, 100 mg of the desired product II was obtained; total 360 mg (1 mM), yield 74%.

To the hydrolysis product 11 (360 mg) in DMSO (20 ml) at 75° C. which was still a heterogeneous mixture, methanesulfonic acid (110 mg in 3 ml of PrOH) was added dropwise at 75° C. Upon addition of the acid the mixture became a homogeneous solution instantaneously. The solution was cooled to room temperature and at this point no solid precipitation was observed. Therefore, most of DMSO was removed in vacuo and THF (10 ml) was added to the residue with stirring. The desired solid product was precipitated, filtered, washed with $Et_2O$ and dried to obtain 395 mg of methanesulfonic acid salt 12; mp 245°-250° (decomp.). $^1H$ NMR ($D_2O$) δ 8.97 (s, 1H), 7.62 (d, J=13 Hz, 1H), 4.0~4.35 (m, 5H), 3.26 (s, 1H), 2.78 (s, 3H), 2.2~2.6 (m, 2H), 2.1 (s, 6H); IR (mineral oil) 3268 (broad), 1722, 1703, 1633, 1600 $cm^{-1}$; HRMS (FAB, M+H) 359.1535 (calcd for $C_{18}H_{20}N_4O_3F$ 359.1519).

EXAMPLE 15

Preparation of (E)-2-(4-(3-carboxy-1-(1,1-dimethylpropargyl)-6-fluoro-1,4-dihydro-4-oxo-7-(1,8-naphthyridine))-1-(N-3-aminopyrrolidinyl)))-2-butnedioic acid, dimethyl ester Dimethyl acetylenedicarboxylate (25 μl, 0.2 mmol) was added to a solution of the amino acid (55 mg, 0.145 mmol) in DMF (2.5 ml). After stirring at 50° C. for 6.5 h, the solvent was evaporated off under a stream of nitrogen. The residue was flash chromatographed (5 g CC-4 silica gel, 2% $MeOH/CH_2Cl_2$, 4 ml fractions), to afford 44 mg of product (60%, fractions 6-10). An analytical sample was recrystallized from EtOAc/hexane. mp 110°-4° C.;

EXAMPLE 16

Preparation of E-2-(4-(3-carboxy-1-(1.1.1.)-pent-1-yl)6-fluoro-1,4-dihydro-4-oxy-7-(1,8-naphthyridine))-1-(N-(3-aminopyrrolidinyl)))-2-butenoic acid, dimethyl ester Dimethyl acetylenedicarboxylate (71 mg) was added to a DMF (3 mL) suspension of the amino acid (165 mg) and the resulting reaction stirred at 55° C. for 2 hours. The reaction was cooled to room temperature and the DMF removed under a stream of N2. The resulting solid was dissolved in $CH_2CH_2$ and filtered. The filtrate was evaporated and the resulting product recrystallized from isopropyl alcohol/ether to yield 152 mg of a white solid. MP 157°-61° C.

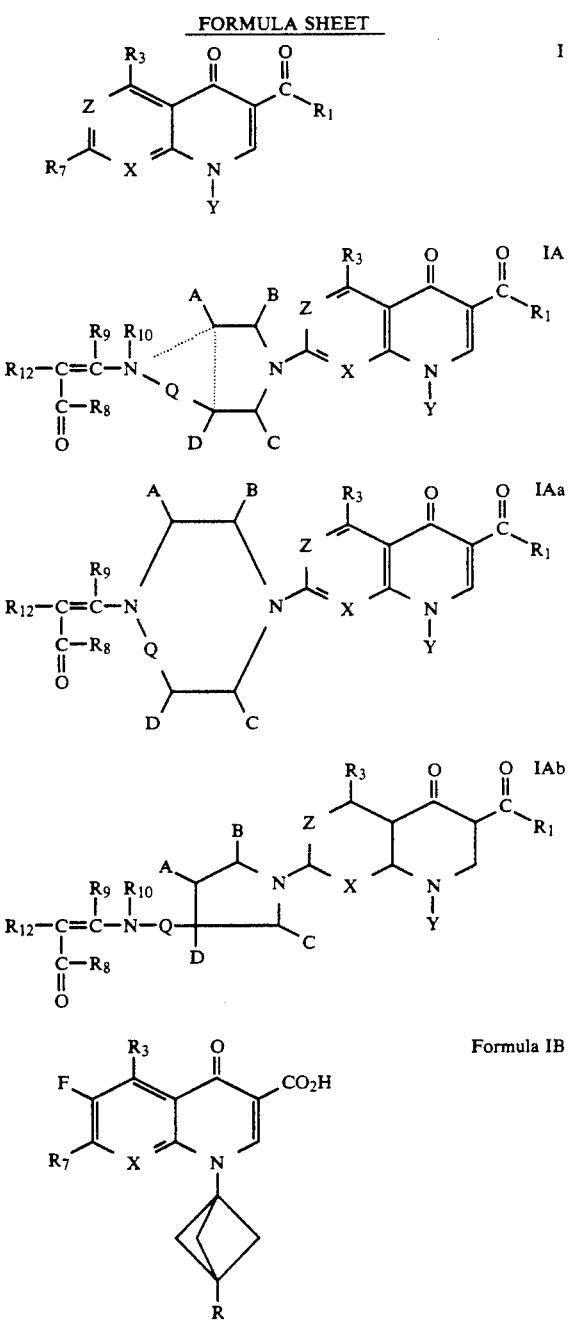

FORMULA SHEET

-continued
FORMULA SHEET
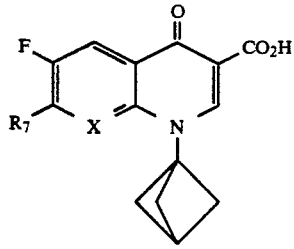
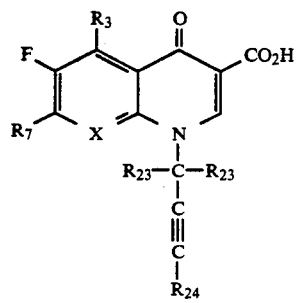
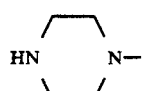
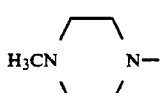
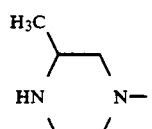
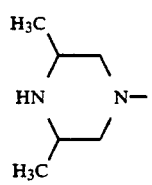
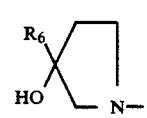
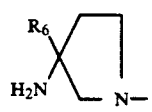
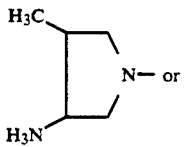
-continued
FORMULA SHEET
Formula IBa
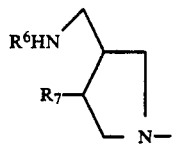
Formula IC
Formula J'
Formula K'
Formula L'
Formula M'
Formula N'
Formula O'
Formula P'
Formula Q'
Formula R'
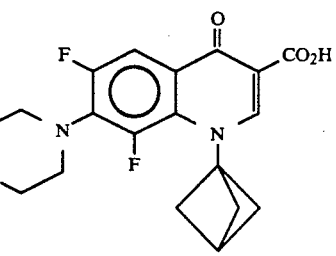
Compound No. 1
m.p. 225–226° C.
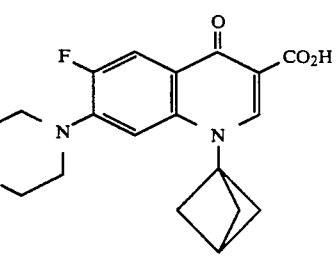
Compound No. 2
m.p. 233–235° C.
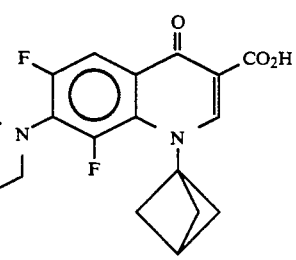
Compound No. 3
m.p. 232–233° C.
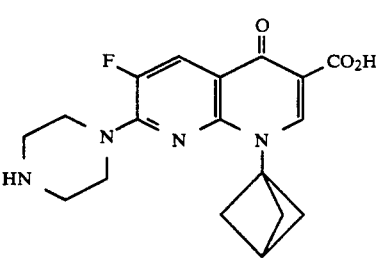
Compound No. 4
mp >250° C.
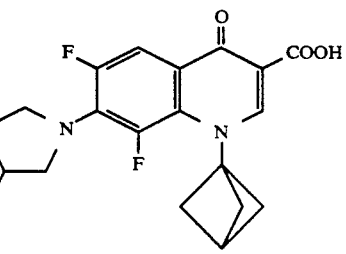
Compound No. 84
m.p. 222–223° C.

-continued
FORMULA SHEET
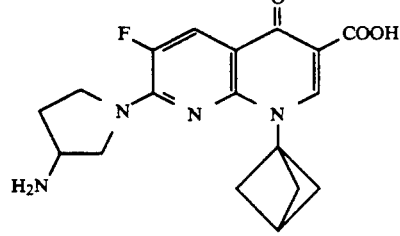
Compound No. 36
m.p. 275° C. dec
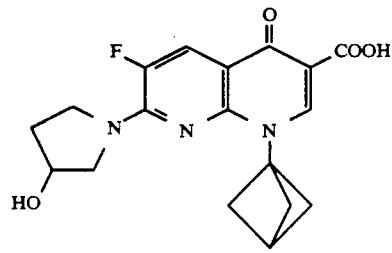
Compound No. 91
m.p. >300° C.
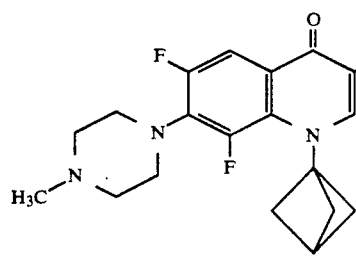
Compound No. 99
m.p. 264–265° C.
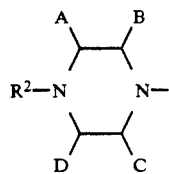
Formula A'
-continued
FORMULA SHEET
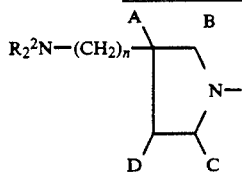  B'
  C'
wherein W is $NR^2$, S or O,
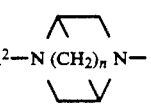  D'
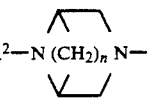  E'
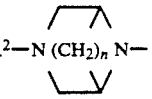  F'
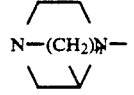  G'
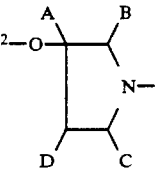  H'
SCHEME 1
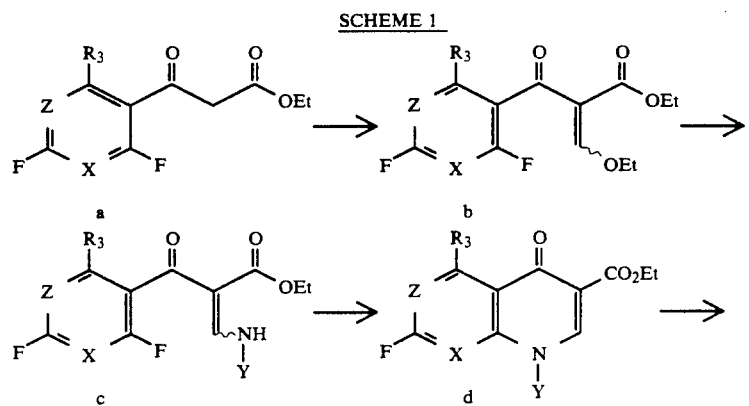

SCHEME 1
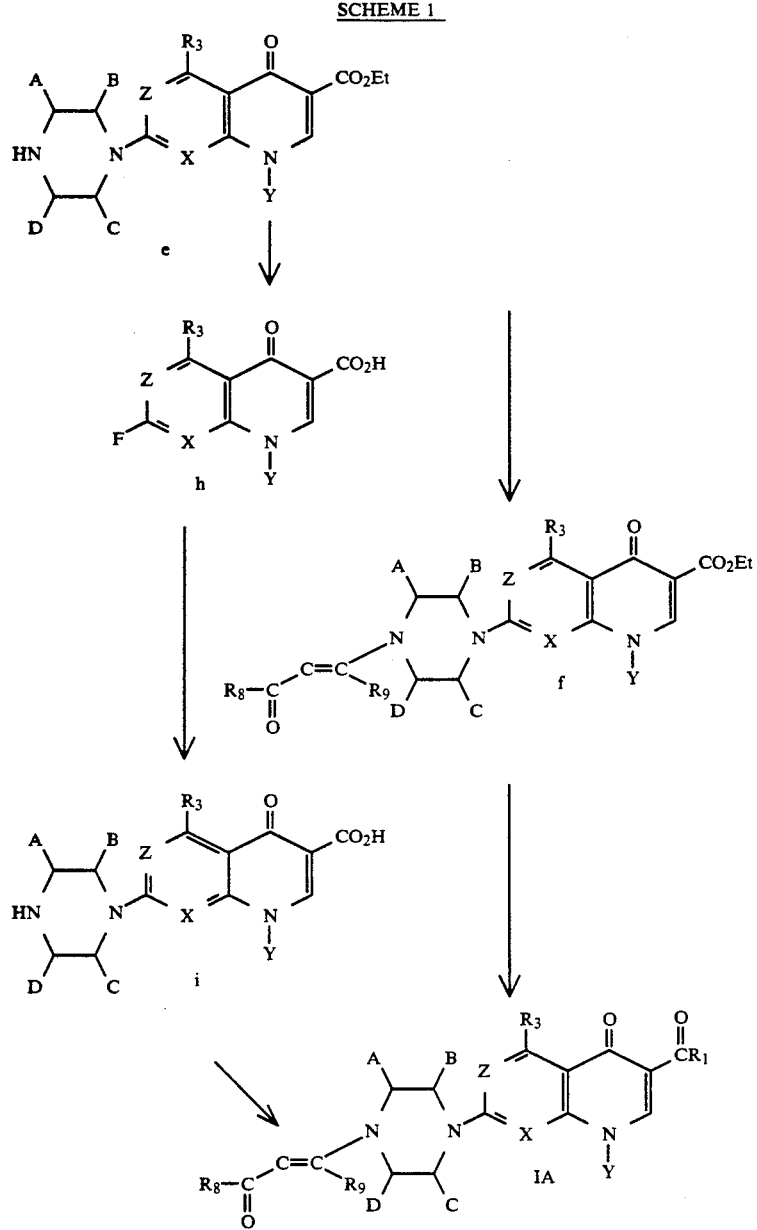
SCHEME 2
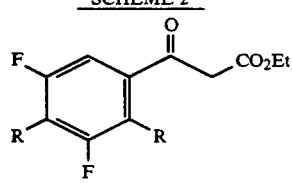
R = F or Cl
-continued
SCHEME 2
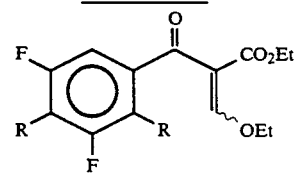

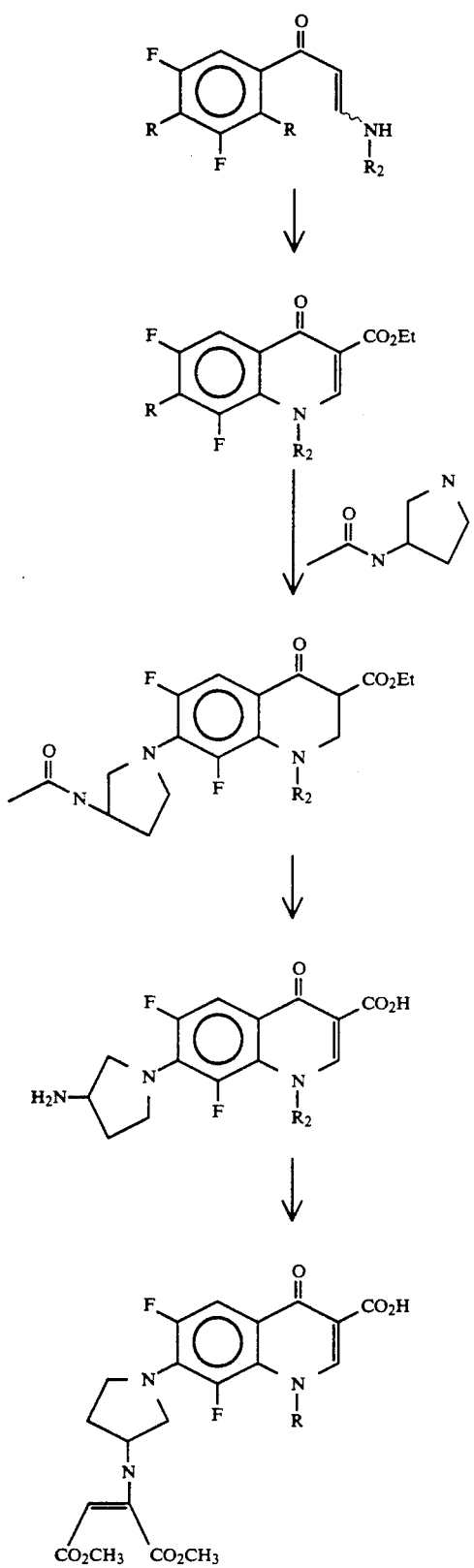
SCHEME 2
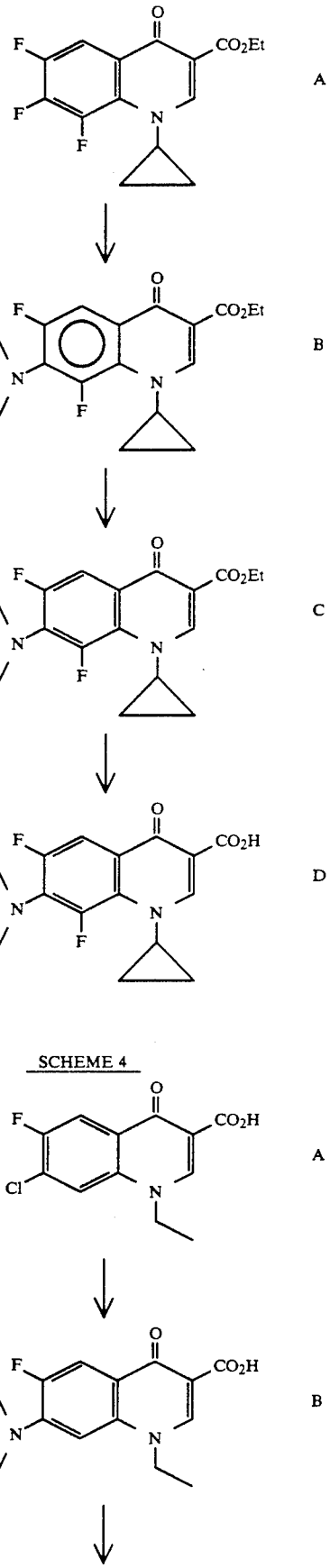
SCHEME 3
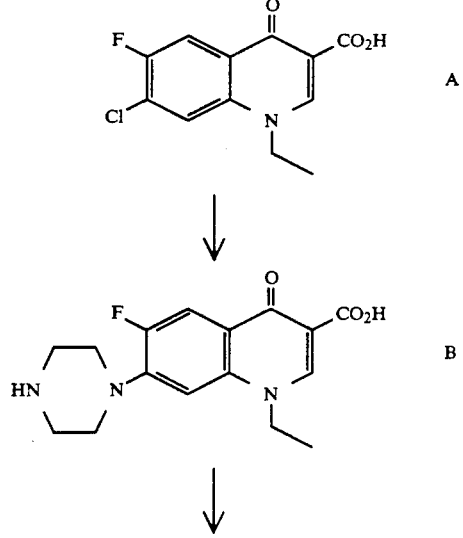
SCHEME 4

-continued
SCHEME 4
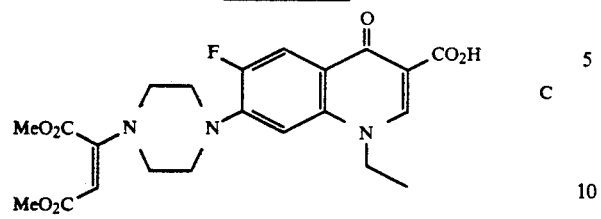
SCHEME 5
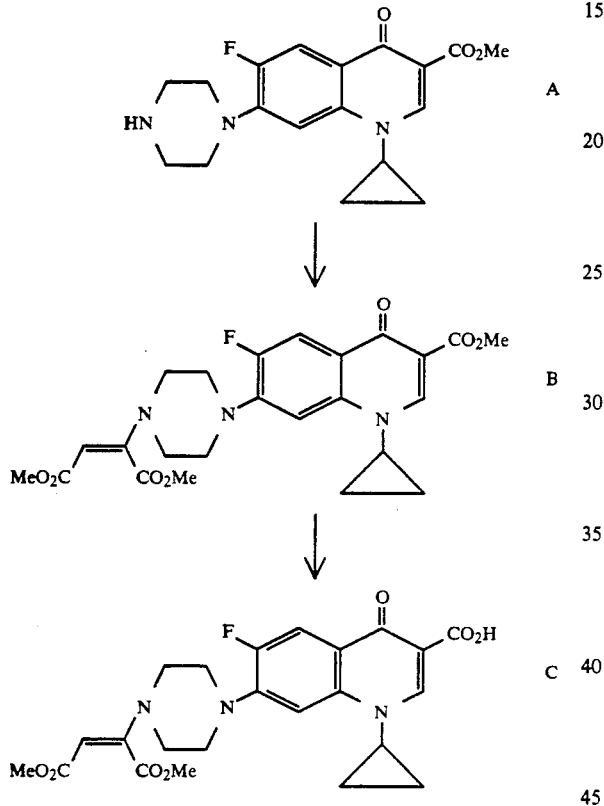
SCHEME 6
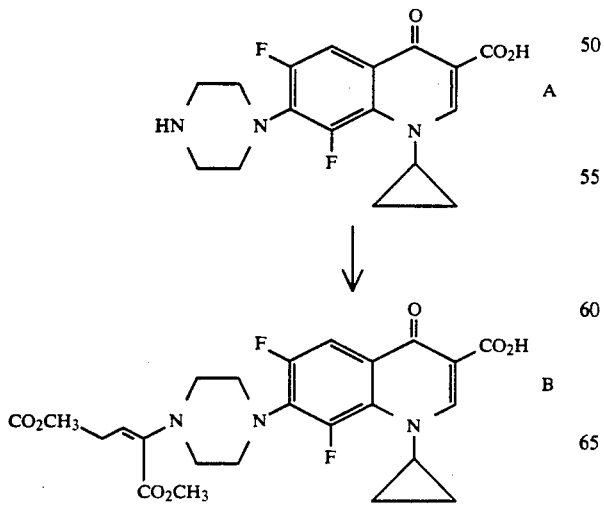
SCHEME 7
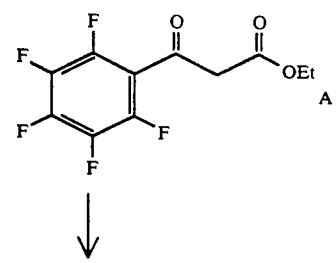
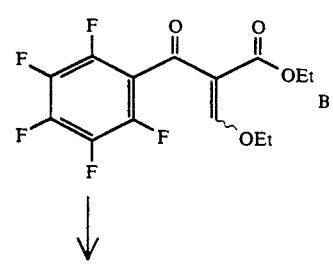
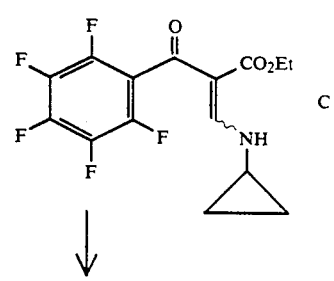
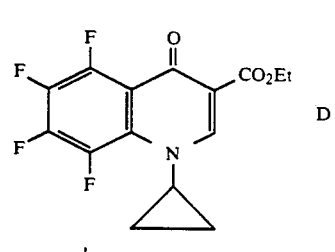
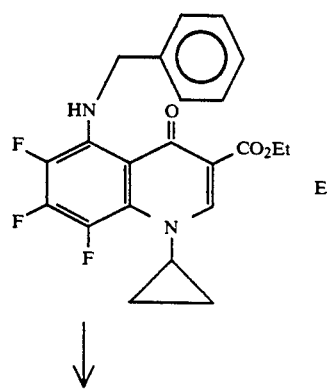

SCHEME 7
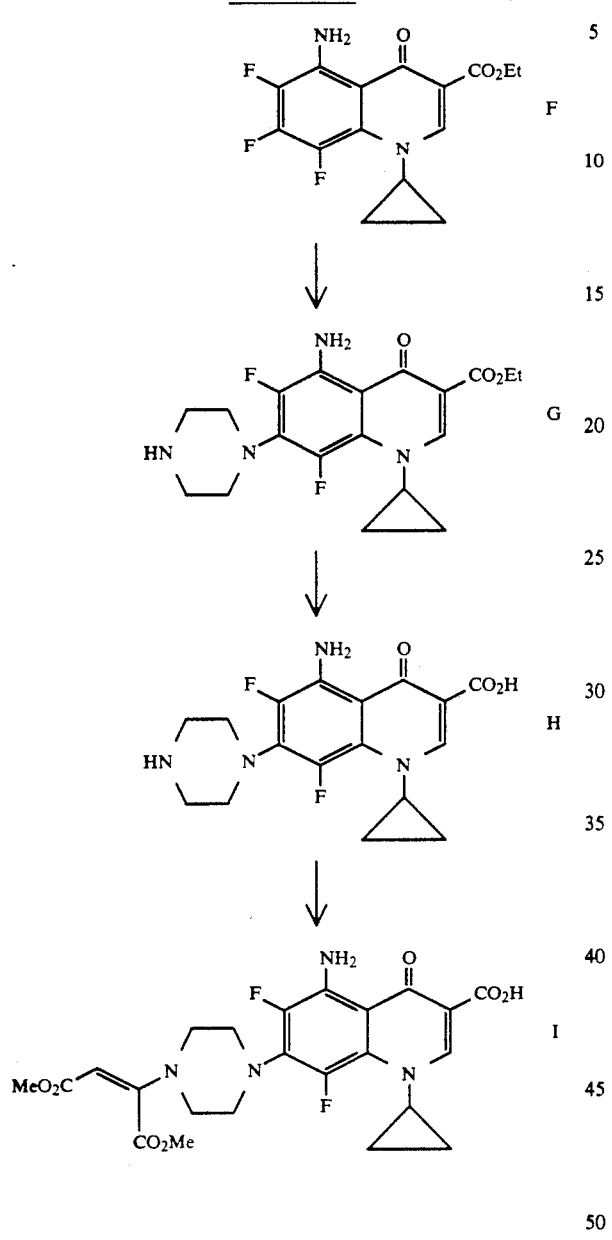
SCHEME 8
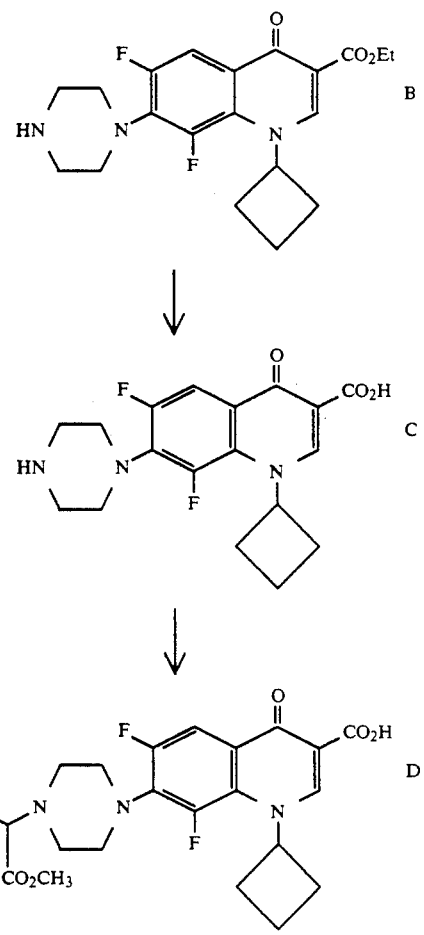
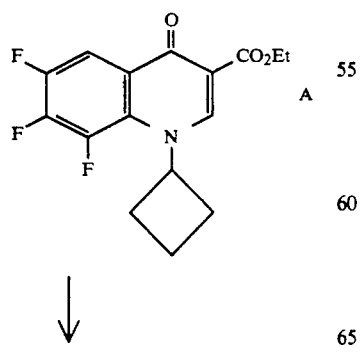
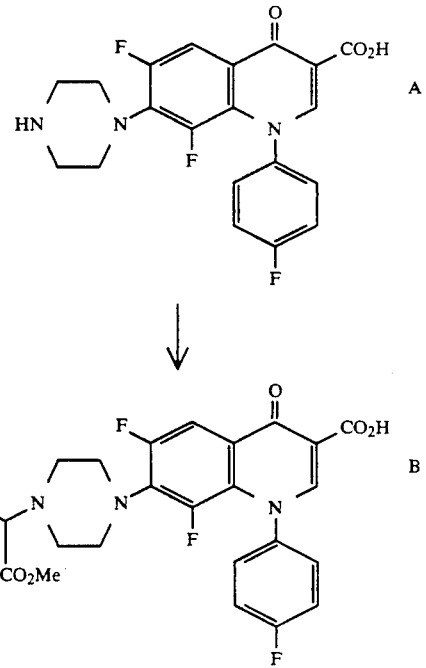

SCHEME 10
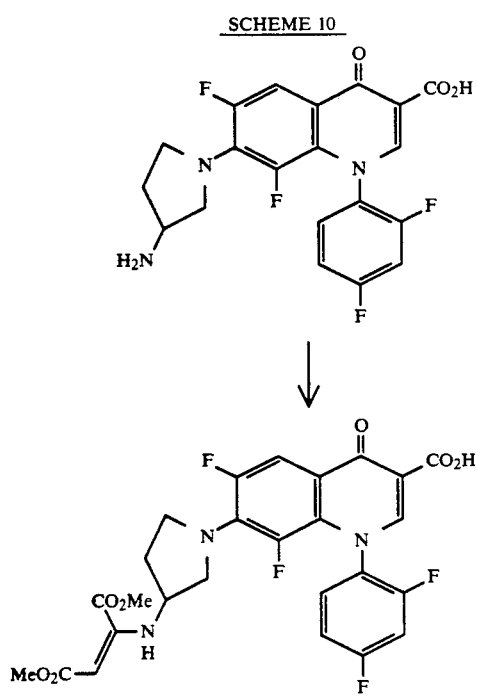
SCHEME 11
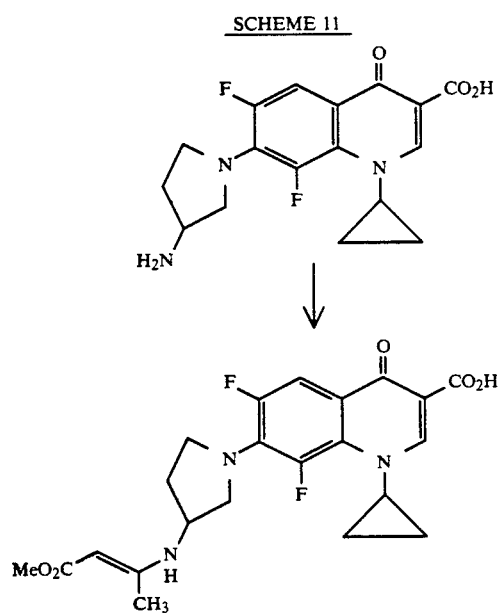
SCHEME 12
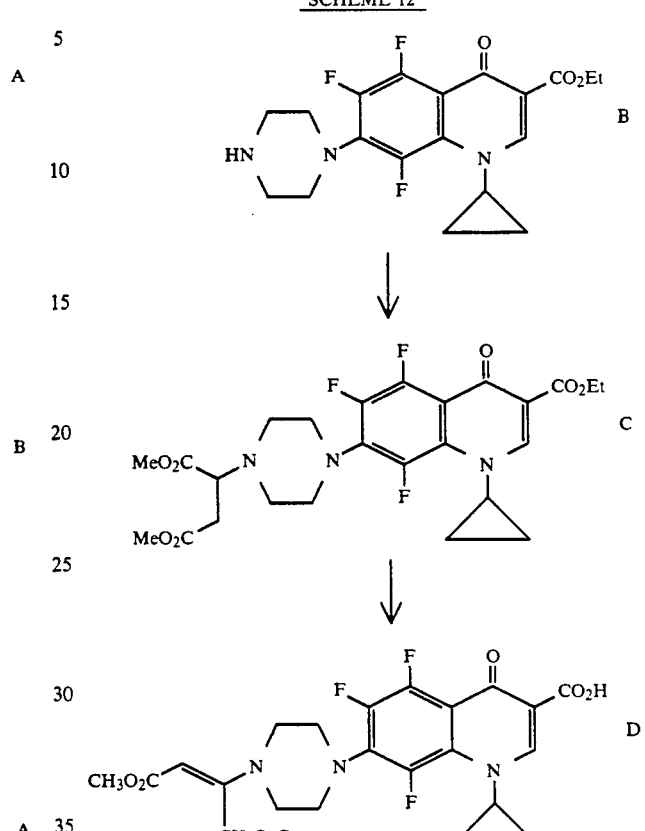
-continued
SCHEME 12
SCHEME 13
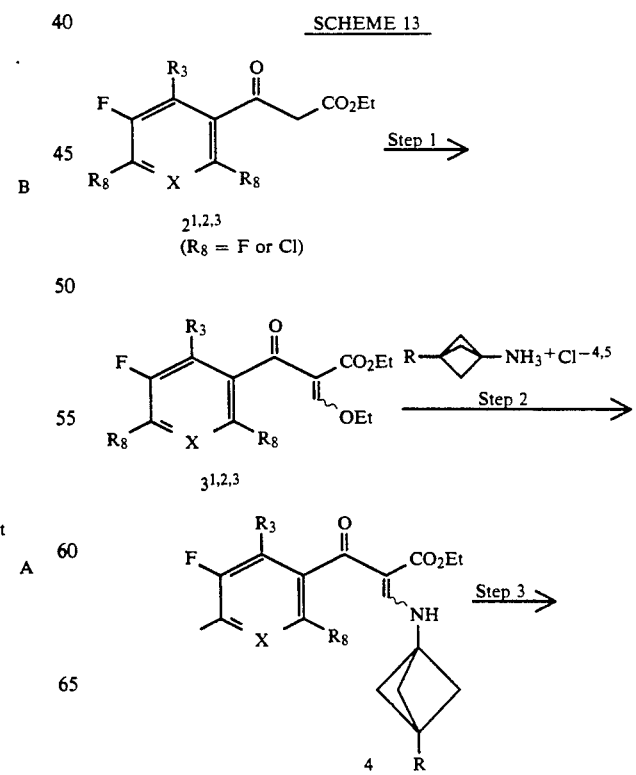

-continued
SCHEME 13
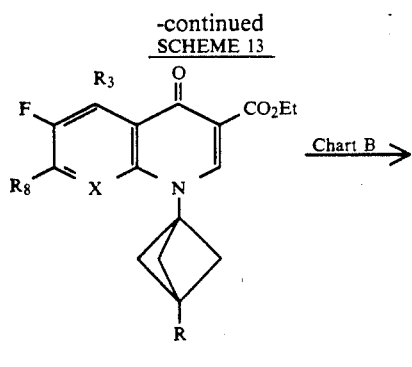
5
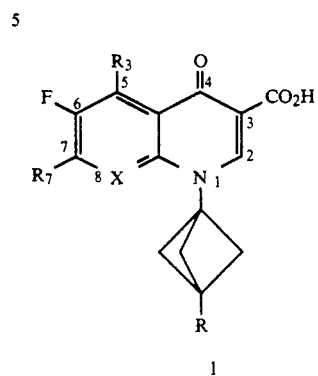
1
SCHEME 15
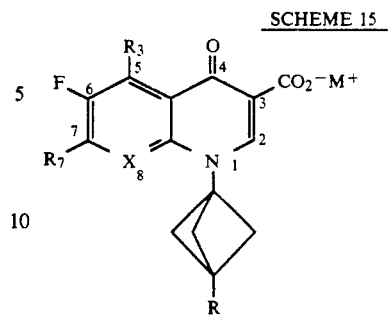
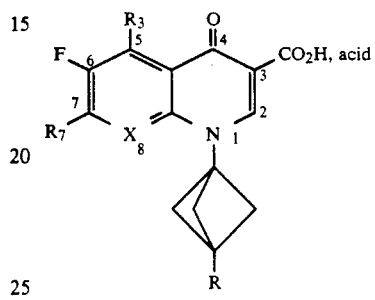
SCHEME 16
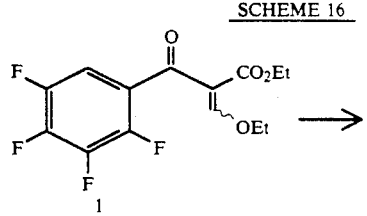
1
SCHEME 14
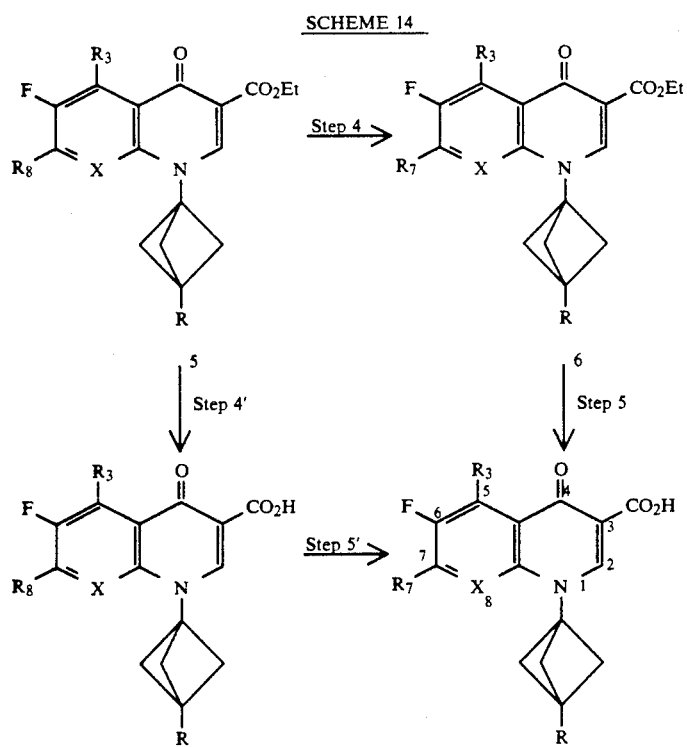

-continued
SCHEME 16

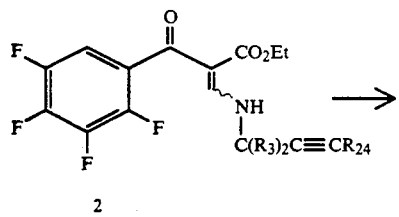
2

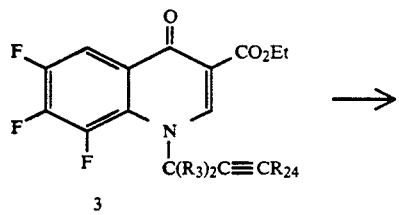
3

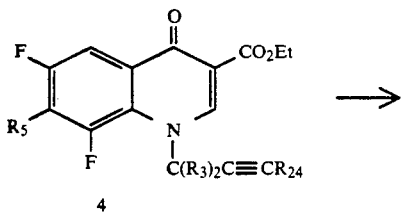
4

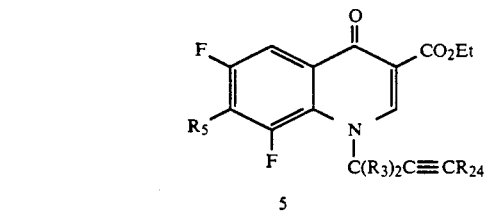
5

SCHEME 17

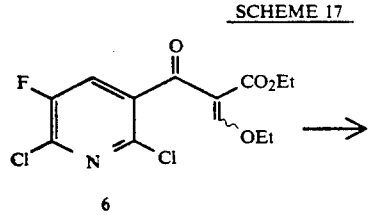
6

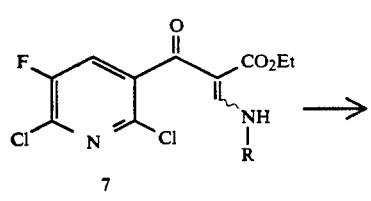
7

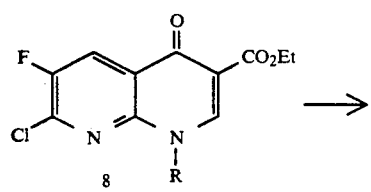
8

-continued
SCHEME 17

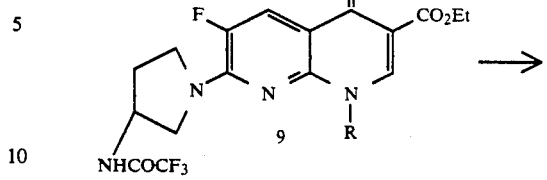
9

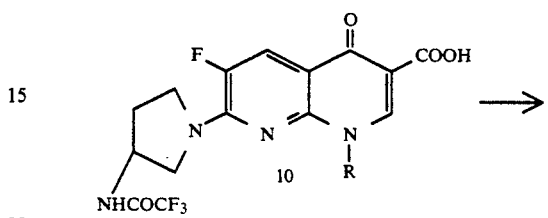
10

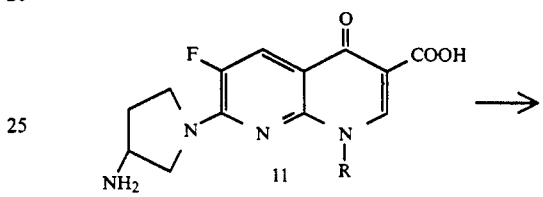
11

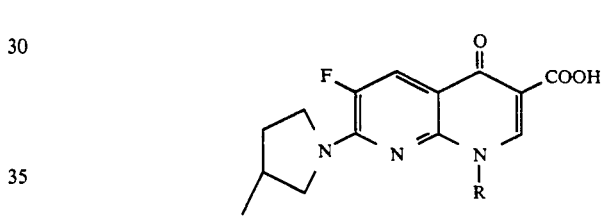
12

R = —C(CH₃)₂C≡CH

TABLE BI
Formula IB

| Cpd # | X  | R₇ |
|-------|-----|------------------------------------------|
| 1     | CF  | 1-piperazinyl |
| 2     | CH  | 1-piperazinyl |
| 3     | CF  | 3-hydroxy-1-pyrrolidinyl |
| 4     | N   | 1-piperazinyl |
| 5     | CH  | 3-phenyl-1-piperazinyl |
| 6     | CH  | 3-amino-3-methylpyrrolidin-1-yl |
| 7     | CH  | 4-methyl-1-piperazinyl |
| 8     | CH  | 2,5-diazabicyclo[2.2.2]octan-2-yl |
| 9     | CH  | 1S,4S-2,5-diazabicyclo[2.2.1]heptan-2-yl |
| 10    | CH  | 3-aminomethyl-1-pyrrolidinyl |
| 11    | CH  | 3-(Ethylamino)methyl-1-pyrrolidinyl |
| 12    | CH  | 3-methyl-1-piperazinyl |
| 13    | CH  | 3,5-dimethyl-1-piperazinyl |
| 14    | CH  | 4-dimethylamino-1-piperazinyl |
| 15    | CH  | 1R,4R-2,5-diazabicyclo[2.2.1]heptan-2-yl |
| 16    | CH  | 4-(1,1-dimethylethyl)-1-piperazinyl |
| 17    | CF  | 3-(ethylamino)methyl-1-pyrrolidinyl |

TABLE B1-continued

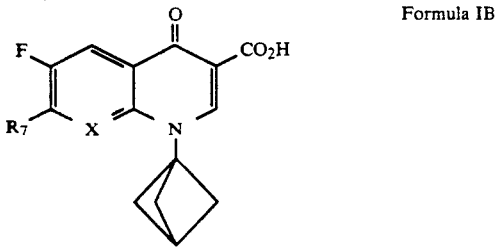

Formula IB

| Cpd # | X | R7 |
|---|---|---|
| 18 | CF | 1R,4R-2,5-diazabicyclo[2.2.1]heptan-2-yl |
| 19 | CH | 3-amino-1-pyrrolidinyl |
| 20 | CH | 8-methyl-3,8-diazabicyclo[3.2.1]octan-3-yl |
| 21 | N | 3-methyl-1-piperazinyl |
| 22 | N | 1S,4S-2,5-diazabicyclo[2.2.1]heptan-2-yl |
| 23 | N | 2,5-diazabicyclo[2.2.2]octan-2-yl |
| 24 | N | 4-(cyclopenten-3-yl)-1-piperazinyl |
| 25 | N | 3-amino-1-pyrrolidinyl |
| 26 | N | 3-(ethylamino)methyl-1-pyrrolidinyl |
| 27 | N | 3-methyl-1-piperazinyl |
| 28 | N | 3,4-dimethyl-1-piperazinyl |
| 29 | N | 3-phenyl-1-piperazinyl |
| 30 | N | 1R,4R-2,5-diazabicyclo[2.2.1]heptan-2-yl |
| 31 | N | 1R,4R-5-methyl-2,5-diazabicyclo[2.2.1]heptan-2-yl |
| 32 | N | 8-methyl-3,8-diazabicyclo[3.2.1]octan-3-yl |
| 33 | N | 3,8-diazabicyclo[3.2.1]octan-3-yl |
| 34 | N | 2-aminomethyl-morpholin-4-yl |
| 35 | N | 3-amino-3-methylpyrrolidin-1-yl |
| 36 | N | 3-amino-1-pyrrolidinyl (racemate) |
| 37 | N | 3-fluoromethyl-piperazin-4-yl |
| 38 | N | 3-aminomethyl-piperazin-4-yl |
| 39 | CH | 3-fluoromethyl-piperazin-4-yl |
| 40 | N | 1,4-diazabicyclo[3.2.1]oct-4-yl |
| 41 | N | 3,8-diazabicyclo[3.2.1]oct-8-yl |
| 42 | N | 3-amino-4-methyl-1-pyrrolidinyl (cis and trans mixture) |
| 43 | N | 4-aminomethyl-3-hydroxy-1-pyrrolidinyl |
| 44 | CH | 4-aminomethyl-3-hydroxy-1-pyrrolidinyl |
| 45 | N | (R)-3-amino-1-pyrrolidinyl |
| 46 | N | (S)-3-amino-1-pyrrolidinyl |
| 47 | N | cis-3-amino-4-methyl-1-pyrrolidinyl |
| 48 | N | trans-3-amino-4-methyl-1-pyrrolidinyl |
| 49 | N | 3-aminomethyl-4-fluoro-1-pyrrolidinyl (cis and trans) |
| 50 | N | 3-aminomethyl-4-fluoro-1-pyrrolidinyl (cis) |
| 51 | N | 3-aminomethyl-4-fluoro-1-pyrrolidinyl (trans) |
| 52 | N | 3-amino-4-fluoro-1-pyrrolidinyl (cis and trans) |
| 53 | N | 3-amino-4-fluoro-1-pyrrolidinyl (cis) |
| 54 | N | 3-amino-4-fluoro-1-pyrrolidinyl (trans) |
| 55 | N | 3-methylamino-1-pyrrolidinyl |
| 56 | N | 3-ethylamino-1-pyrrolidinyl |
| 57 | N | 3-dimethylamino-1-pyrrolidinyl |
| 58 | N | 3-(R)-(4-methylpiperazin-1-yl)-1-pyrrolidinyl |
| 59 | N | 3-(R)-N',N'-dimethylhydrazino-pyrrolidin-1-yl |
| 60 | N | 3-(iminomethyl)amino-1-pyrrolidinyl |
| 61 | N | 3-imino-1-pyrrolidinyl |
| 62 | N | 3-(aminoiminomethyl)amino-1-pyrrolidinyl |
| 63 | N | 2-methyl-4-amino-1-pyrrolidinyl (cis and trans) |
| 64 | N | 2-methyl-4-amino-1-pyrrolidinyl (cis) |
| 65 | N | 2-methyl-4-amino-1-pyrrolidinyl (trans) |
| 66 | N | 3-hydroxyamino-1-pyrrolidinyl |
| 67 | N | 3-hydroxyamino-1-pyrrolidinyl |
| 68 | N | 3-(N-cyano)amino-1-pyrrolidinyl |
| 69 | N | 2,6-diazabicyclo[3.2.0]heptan-6-yl |
| 70 | N | 2-methyl-2,6-diazabicyclo[3.2.0]heptan-6-yl |
| 71 | N | 3-(R)-amino-4-(R)-ethyl-1-pyrrolidinyl |
| 72 | N | 3-(R)-amino-4-(S)-ethyl-1-pyrrolidinyl |
| 73 | N | 3-(S)-amino-4-(R)-ethyl-1-pyrrolidinyl |
| 74 | N | 3-(S)-amino-4-(S)-ethyl-1-pyrrolidinyl |
| 75 | N | 2-(R)-methyl-3-(R)-amino-1-pyrrolidinyl |
| 76 | N | 2-(R)-methyl-3-(S)-amino-1-pyrrolidinyl |
| 77 | N | 2-(S)-methyl-3-(R)-amino-1-pyrrolidinyl |
| 78 | N | 2-(S)-methyl-3-(S)-amino-1-pyrrolidinyl |
| 79 | N | 3-(R)-amino-4-(R)-phenyl-1-pyrrolidinyl |
| 80 | N | 3-(R)-amino-4-(S)-phenyl-1-pyrrolidinyl |

TABLE B1-continued

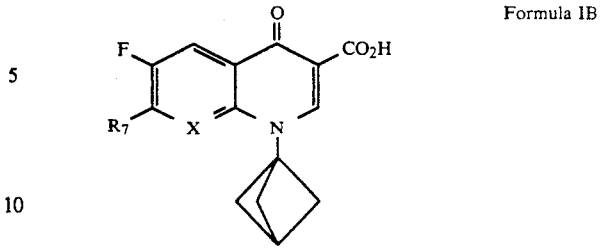

Formula IB

| Cpd # | X | R7 |
|---|---|---|
| 81 | N | 3-(S)-amino-4-(R)-phenyl-1-pyrrolidinyl |
| 82 | N | 3-(S)-amino-4-(S)-phenyl-1-pyrrolidinyl |
| 83 | CF | 4-(cyclopenten-3-yl)-1-piperazinyl |
| 84 | CF | 3-amino-1-pyrrolidinyl (racemate) |
| 85 | CF | 3-amino-4-methyl-pyrrolidin-1-yl |
| 86 | CH | 3-hydroxy-1-pyrrolidinyl |
| 87 | CH | 3-amino-4-methyl-pyrrolidin-1-yl |
| 88 | N | 3,5-dimethyl-1-piperazinyl |
| 89 | N | 3-hydroxy-3-phenylpyrrolidin-1-yl |
| 90 | N | 3-amino-3-phenylpyrrolidin-1-yl |
| 91 | N | 3-hydroxy-1-pyrrolidinyl (racemate) |
| 92 | N | 3-hydroxy-3-methylpyrrolidin-1-yl |
| 93 | CH | 3-(2-butenedioic acid, dimethyl ester)amino-1-pyrrolidinyl |
| 94 | CH | 4-(2-butenedioic acid, dimethyl ester)-1-piperazinyl |
| 95 | CH | 3-(2-butanedioic acid)amino-1-pyrrolidinyl |
| 96 | CH | 3-(2-butanedioic acid)-1-piperazinyl |
| 97 | CH | 3-(2-butanedioic acid, dimethyl ester)amino-1-pyrrolidinyl |
| 98 | CH | 3-(2-butanedioic acid, dimethyl ester)-1-piperazinyl |
| 99 | CF | 4-methyl-1-piperazinyl |

TABLE B2

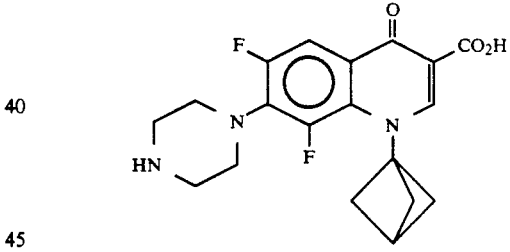

MIC Medium  MHA
Control  Ciprofloxacin

MINIMUM INHIBITORY CONCENTRATION (mcg per ml)

| Organism Name | Cult No. | Compound No. 1 | Control |
|---|---|---|---|
| Staphylococcus aureus | 3665 | 0.5 | 1 |
| Staphylococcus aureus | 6685 | 0.5 | 0.25 |
| Staphylococcus aureus | 9213 | 1 | 1 |
| Staphylococcus aureus | 9218 | 0.5 | 0.5 |
| Staphylococcus aureus | 9271 | 0.5 | 0.5 |
| Staphylococcus epidermidis | 30031 | 0.25 | 0.125 |
| Streptococcus faecalis | 9217 | 2 | 0.5 |
| Streptococcus pneumoniae | 41 | 2 | 0.5 |
| Streptococcus pyogenes | 152 | 2 | 0.25 |
| Acinetobacter calcoaceticus | 12170 | 0.25 | 0.25 |
| Citerobacter freundii | 3507 | 0.06 | <0.008 |
| Enterobacter cloacae | 9382 | 0.06 | 0.015 |
| Escherichia coli | 6674 | 0.06 | 0.015 |
| Escherichia coli | 9952 | 0.06 | 0.015 |
| Escherichia coli | 9451 | 0.06 | 0.015 |
| Escherichia coli | 9855 | 0.06 | 0.015 |
| Klebsiella pneumoniae | 12081 | 0.125 | 0.03 |
| Proteus penneri | 9679 | 0.5 | 0.015 |
| Pseudomonas aeruginosa | 6676 | 2 | 0.5 |
| Pseudomonas aeruginosa | 9191 | 1 | 0.25 |
| Pseudomonas aeruginosa | 12120 | 1 | 0.125 |

TABLE B2-continued

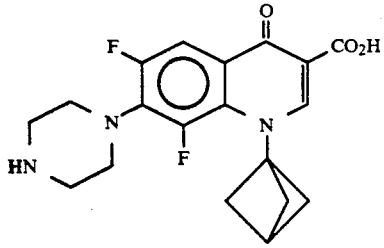

MIC Medium  MHA
Control  Ciprofloxacin

MINIMUM INHIBITORY CONCENTRATION (mcg per ml)

| Organism Name | Cult No. | Compound No. 1 | Control |
|---|---|---|---|
| Serratia marcescens | 6888 | 0.25 | 0.06 |

Cultures numbered less than 30000 are from the Upjohn culture collection (UC); cultures numbered 30000 or greater are non-UC cultures.

TABLE B3

MIC Medium  MHA
Control  Ciprofloxacin

MINIMUM INHIBITORY CONCENTRATION (mcg per ml)

| Organism Name | Cult No. | Compound No. 2 | Cipro |
|---|---|---|---|
| Staphylococcus aureus | 6685 | 0.5 | 0.25 |
| Staphylococcus aureus | 9213 | 1 | 1 |
| Staphylococcus aureus | 9218 | 1 | 0.5 |
| Staphylococcus aureus | 9271 | 1 | 0.5 |
| Staphylococcus epidermidis | 30031 | 0.5 | 0.125 |
| Streptococcus faecalis | 9217 | 4 | 0.5 |
| Streptococcus pneumoniae | 41 | 4 | 0.5 |
| Streptococcus pyogenes | 152 | 2 | 0.25 |
| Acinetobacter calcoaceticus | 12170 | 0.5 | 0.25 |
| Citerobacter freundii | 3507 | 0.06 | <0.008 |
| Enterobacter cloacae | 9382 | 0.125 | 0.015 |
| Escherichia coli | 6674 | 0.125 | 0.015 |
| Escherichia coli | 9952 | 0.125 | 0.015 |
| Escherichia coli | 9451 | 0.125 | 0.015 |
| Escherichia coli | 9855 | 0.125 | 0.015 |
| Klebsiella pneumoniae | 12081 | 0.25 | 0.03 |
| Proteus penneri | 9679 | 0.5 | 0.03 |
| Pseudomonas aeruginosa | 6676 | 4 | 0.5 |
| Pseudomonas aeruginosa | 9191 | 2 | 0.25 |
| Pseudomonas aeruginosa | 12120 | 1 | 0.125 |
| Serratia marcescens | 6888 | 0.5 | 0.06 |

Cultures numbered less than 30000 are from the Upjohn culture collection (UC); cultures numbered 30000 or greater are non-UC cultures.

TABLE B4

MIC Medium  MHA
Control  Ciprofloxacin

MINIMUM INHIBITORY CONCENTRATION (mcg per ml)

| Organism Name | Cult No. | Compound No. 3 | Cipro |
|---|---|---|---|
| Staphylococcus aureus | 6685 | 0.06 | 0.25 |
| Staphylococcus aureus | 9213 | 0.125 | 1 |
| Staphylococcus aureus | 9218 | 0.125 | 0.5 |
| Staphylococcus aureus | 9271 | 0.125 | 0.5 |
| Staphylococcus epidermidis | 30031 | 0.125 | 0.125 |
| Streptococcus faecalis | 9217 | 1 | 0.5 |
| Streptococcus pneumoniae | 41 | 1 | 0.5 |
| Streptococcus pyogenes | 152 | 2 | 0.25 |
| Acinetobacter calcoaceticus | 12170 | 0.25 | 0.25 |
| Citerobacter freundii | 3507 | 0.25 | <0.008 |
| Enterobacter cloacae | 9382 | 0.25 | 0.015 |
| Escherichia coli | 6674 | 0.25 | 0.015 |
| Escherichia coli | 9952 | 0.125 | 0.015 |
| Escherichia coli | 9451 | 0.25 | 0.015 |
| Escherichia coli | 9855 | 0.25 | 0.015 |
| Klebsiella pneumoniae | 12081 | 0.5 | 0.03 |
| Proteus penneri | 9679 | 0.5 | 0.03 |
| Pseudomonas aeruginosa | 6676 | 2 | 0.5 |
| Pseudomonas aeruginosa | 9191 | 2 | 0.25 |
| Pseudomonas aeruginosa | 12120 | 1 | 0.125 |
| Serratia marcescens | 6888 | 1 | 0.06 |

Cultures numbered less than 30000 are from the Upjohn culture collection (UC); cultures numbered 30000 or greater are non-UC cultures.

TABLE B5

MIC Medium  MHA
Control  Ciprofloxacin

MINIMUM INHIBITORY CONCENTRATION (mcg per ml)

| Organism Name | Cult No. | Compound No. 4 | Cipro |
|---|---|---|---|
| Staphylococcus aureus | 6685 | 0.25 | 0.25 |
| Staphylococcus aureus | 9213 | 0.5 | 1 |
| Staphylococcus aureus | 9218 | 0.5 | 0.5 |
| Staphylococcus aureus | 9271 | 0.5 | 0.5 |
| Staphylococcus epidermidis | 30031 | 0.25 | 0.125 |
| Streptococcus faecalis | 9217 | 2 | 0.5 |
| Streptococcus pneumoniae | 41 | 2 | 0.5 |
| Streptococcus pyogenes | 152 | 2 | 0.25 |
| Acinetobacter calcoaceticus | 12170 | 0.25 | 0.25 |
| Citerobacter freundii | 3507 | 0.06 | <0.008 |
| Enterobacter cloacae | 9382 | 0.06 | 0.015 |
| Escherichia coli | 6674 | 0.06 | 0.015 |
| Escherichia coli | 9952 | 0.06 | 0.015 |
| Escherichia coli | 9451 | 0.06 | 0.015 |
| Escherichia coli | 9855 | 0.06 | 0.015 |
| Klebsiella pneumoniae | 12081 | 0.125 | 0.03 |
| Proteus penneri | 9679 | 0.5 | 0.03 |
| Pseudomonas aeruginosa | 6676 | 2 | 0.5 |
| Pseudomonas aeruginosa | 9191 | 1 | 0.25 |
| Pseudomonas aeruginosa | 12120 | 0.5 | 0.125 |
| Serratia marcescens | 6888 | 0.25 | 0.06 |

Cultures numbered less than 30000 are from the Upjohn culture collection (UC); cultures numbered 30000 or greater are non-UC cultures.

TABLE B6

MIC Medium  MHA
Control  Ciprofloxacin

MINIMUM INHIBITORY CONCENTRATION (mcg per ml)

| Organism Name | Cult No. | Compound No. 99 | Cipro |
|---|---|---|---|
| Staphylococcus aureus | 6685 | 0.5 | 0.125 |
| Staphylococcus aureus | 9213 | 0.5 | 0.5 |
| Staphylococcus aureus | 9218 | 0.5 | 0.25 |
| Staphylococcus aureus | 9271 | 0.5 | 0.5 |
| Staphylococcus epidermidis | 30031 | 0.5 | 0.125 |
| Streptococcus faecalis | 9217 | 4 | 0.5 |
| Streptococcus pneumoniae | 41 | 2 | 0.25 |
| Streptococcus pyogenes | 152 | 2 | 0.125 |
| Acinetobacter calcoaceticus | 12170 | 0.125 | 0.125 |
| Citerobacter freundii | 3507 | 0.25 | <0.008 |
| Enterobacter cloacae | 9382 | 0.25 | 0.015 |
| Escherichia coli | 6674 | 0.25 | 0.015 |
| Escherichia coli | 9952 | 0.125 | <0.008 |
| Escherichia coli | 9451 | 0.255 | 0.015 |
| Escherichia coli | 9855 | 0.25 | 0.015 |
| Klebsiella pneumoniae | 12081 | 0.5 | 0.03 |
| Proteus penneri | 9679 | 2 | 0.015 |
| Pseudomonas aeruginosa | 6676 | 4 | 0.5 |
| Pseudomonas aeruginosa | 9191 | 4 | 0.125 |
| Pseudomonas aeruginosa | 12120 | 2 | 0.125 |
| Serratia marcescens | 6888 | 1 | 0.06 |

Cultures numbered less than 30000 are from the Upjohn culture collection (UC); cultures numbered 30000 or greater are non-UC cultures.

TABLE B7

MIC Medium  MHA
Control  Ciprofloxacin

MINIMUM INHIBITORY CONCENTRATION (mcg per ml)

| Organism Name | Cult No. | Compound No. 91 | Cipro |
|---|---|---|---|
| Staphylococcus aureus | 6685 | 0.06 | 0.25 |
| Staphylococcus aureus | 9213 | 0.125 | 1 |
| Staphylococcus aureus | 9218 | 0.125 | 0.5 |
| Staphylococcus aureus | 9271 | 0.125 | 0.5 |
| Staphylococcus epidermidis | 30031 | 0.125 | 0.125 |
| Streptococcus faecalis | 9217 | 1 | 0.5 |
| Streptococcus pneumoniae | 41 | 1 | 0.5 |
| Streptococcus pyogenes | 152 | 2 | 0.25 |
| Acinetobacter calcoaceticus | 12170 | 0.5 | 0.25 |
| Citerobacter freundii | 3507 | 0.25 | <0.008 |
| Enterobacter cloacae | 9382 | 0.25 | 0.015 |
| Escherichia coli | 6674 | 0.125 | 0.015 |
| Escherichia coli | 9952 | 0.125 | 0.015 |
| Escherichia coli | 9451 | 0.25 | 0.015 |
| Escherichia coli | 9855 | 0.25 | 0.03 |
| Klebsiella pneumoniae | 12081 | 0.5 | 0.03 |
| Proteus penneri | 9679 | 1 | 0.03 |
| Pseudomonas aeruginosa | 6676 | 4 | 0.5 |
| Pseudomonas aeruginosa | 9191 | 2 | 0.125 |
| Pseudomonas aeruginosa | 12120 | 2 | 0.125 |
| Serratia marcescens | 6888 | 1 | 0.06 |

Cultures numbered less than 30000 are from the Upjohn culture collection (UC); cultures numbered 30000 or greater are non-UC cultures.

TABLE B8

MIC Medium  MHA
Control  Ciprofloxacin

MINIMUM INHIBITORY CONCENTRATION (mcg per ml)

| Organism Name | Cult No. | Compound No. 36 | Cipro |
|---|---|---|---|
| Staphylococcus aureus | 6685 | 0.125 | 0.25 |
| Staphylococcus aureus | 9213 | 0.125 | 1 |
| Staphylococcus aureus | 9218 | 0.125 | 0.5 |
| Staphylococcus aureus | 9271 | 0.125 | 0.5 |
| Staphylococcus epidermidis | 30031 | 0.06 | 0.125 |
| Streptococcus faecalis | 9217 | 0.5 | 0.5 |
| Streptococcus pneumoniae | 41 | 0.5 | 0.5 |
| Streptococcus pyogenes | 152 | 0.25 | 0.25 |
| Acinetobacter calcoaceticus | 12170 | 0.125 | 0.25 |
| Citerobacter freundii | 3507 | 0.03 | <0.008 |
| Enterobacter cloacae | 9382 | 0.03 | 0.015 |
| Escherichia coli | 6674 | 0.03 | 0.015 |
| Escherichia coli | 9952 | 0.03 | 0.015 |
| Escherichia coli | 9451 | 0.03 | 0.015 |
| Escherichia coli | 9855 | 0.06 | 0.03 |
| Klebsiella pneumoniae | 12081 | 0.06 | 0.03 |

TABLE B8-continued

MIC Medium  MHA
Control  Ciprofloxacin

MINIMUM INHIBITORY CONCENTRATION (mcg per ml)

| Organism Name | Cult No. | Compound No. 36 | Cipro |
|---|---|---|---|
| Proteus penneri | 9679 | 0.25 | 0.03 |
| Pseudomonas aeruginosa | 6676 | 1 | 0.5 |
| Pseudomonas aeruginosa | 9191 | 0.5 | 0.125 |
| Pseudomonas aeruginosa | 12120 | 0.25 | 0.125 |
| Serratia marcescens | 6888 | 0.125 | 0.06 |

Cultures numbered less than 30000 are from the Upjohn culture collection (UC); cultures numbered 30000 or greater are non-UC cultures.

TABLE B9

MIC Medium  MHA
Control  Ciprofloxacin

MINIMUM INHIBITORY CONCENTRATION (mcg per ml)

| Organism Name | Cult No. | Compound No. 84 | Cipro |
|---|---|---|---|
| Staphylococcus aureus | 6685 | 0.06 | 0.25 |
| Staphylococcus aureus | 9213 | 0.125 | 1 |
| Staphylococcus aureus | 9218 | 0.125 | 0.5 |
| Staphylococcus aureus | 9271 | 0.125 | 0.5 |
| Staphylococcus epidermidis | 30031 | 0.125 | 0.125 |
| Streptococcus faecalis | 9217 | 0.5 | 0.5 |
| Streptococcus pneumoniae | 41 | 0.5 | 0.5 |
| Streptococcus pyogenes | 152 | 0.25 | 0.25 |
| Acinetobacter calcoaceticus | 12170 | 0.125 | 0.25 |
| Citerobacter freundii | 3507 | 0.36 | <0.008 |
| Enterobacter cloacae | 9382 | 0.06 | 0.015 |
| Escherichia coli | 6674 | 0.03 | 0.015 |
| Escherichia coli | 9952 | 0.03 | 0.015 |
| Escherichia coli | 9451 | 0.06 | 0.015 |
| Escherichia coli | 9855 | 0.06 | 0.03 |
| Klebsiella pneumoniae | 12081 | 0.06 | 0.03 |
| Proteus penneri | 9679 | 0.25 | 0.03 |
| Pseudomonas aeruginosa | 6676 | 1 | 0.5 |
| Pseudomonas aeruginosa | 9191 | 0.5 | 0.125 |
| Pseudomonas aeruginosa | 12120 | 0.5 | 0.125 |
| Serratia marcescens | 6888 | 0.125 | 0.06 |

Cultures numbered less than 30000 are from the Upjohn culture collection (UC); cultures numbered 30000 or greater are non-UC cultures.

TABLE CI

| Organism | UC*# | Minimum Inhibitory Concentration-MCG per mL* | | | | | Ciprofloxacin |
|---|---|---|---|---|---|---|---|
| | | A | B | C | D | E | |
| S. aureus | 6685 | 2 | 0.25 | 32 | 4 | 0.125 | 0.25 |
| S. aureus | 9213 | 4 | 0.5 | 32 | 8 | 0.25 | 1 |
| S. aureus | 9218 | 2 | 0.5 | 32 | 8 | 0.25 | 0.5 |
| S. aureus | 9271 | 2 | 0.5 | 32 | 8 | 0.25 | 0.5 |
| S. epidermidis | 30031 | 1 | 0.25 | 16 | 2 | 0.125 | 0.06 |
| S. faecalis | 9217 | 8 | 2 | >64 | 32 | 1 | 0.5 |
| S. pneumoniae | 41 | 8 | 2 | >64 | 32 | 0.5 | 0.5 |
| S. pyogenes | 152 | 8 | 1 | 32 | 16 | 0.25 | 0.25 |
| A. calcoaceticus | 12170 | 1 | 0.5 | 8 | 4 | 0.25 | 0.25 |
| C. freundii | 3507 | 0.25 | 0.125 | 1 | 0.5 | 0.06 | <0.008 |
| E. cloacae | 9382 | 0.25 | 0.25 | 1 | 1 | 0.06 | 0.015 |
| E. coli | 6674 | 0.25 | 0.125 | 1 | 1 | 0.06 | 0.015 |
| E. coli | 9952 | 0.25 | 0.125 | 1 | 0.5 | 0.06 | <0.008 |
| E. coli | 9451 | 0.25 | 0.125 | 2 | 0.5 | 0.06 | 0.015 |
| E. coli | 9855 | 0.25 | 0.25 | 2 | 2 | 0.06 | 0.03 |
| K. pneumoniae | 12081 | 0.5 | 0.25 | 2 | 1 | 0.125 | 0.03 |
| P. penneri | 9679 | 1 | 1 | 1 | 0.5 | 0.5 | 0.015 |
| Ps. aeruginosa | 6676 | 4 | 2 | 16 | 8 | 2 | 0.5 |
| Ps. aeruginosa | 9191 | 2 | 2 | 8 | 8 | 1 | 0.125 |
| Ps. aeruginosa | 12120 | 2 | 1 | 8 | 4 | 0.5 | 0.125 |
| S. marcescens | | 0.5 | 2 | 1 | 0.25 | 0.06 | |

We claim:

1. The compound which is structurally represented by the formula (IA):

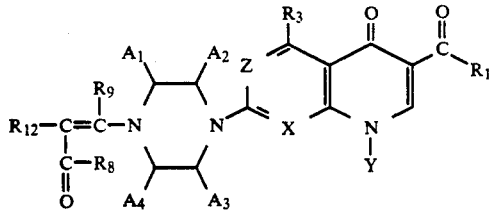

and therapeutically acceptable salts thereof wherein
$R_1$ is hydrogen or hydroxyl;
Y is $C_1$–$C_{10}$ alkyl, $C_3$–$C_{10}$ cycloalkyl, a phenyl, or a substituted phenyl wherein the substituent on the phenyl group is one, two or three of $C_1$–$CH_{10}$ alkyl, halogen, hydroxyl, hydrogen or a combination thereof, or $C_2$–$C_4$ alkylene wherein each carbon atom may be substituted with fluorine;
$R_3$ is hydrogen, halogen amine or hydroxyl;
$A_1$, $A_2$, $A_3$, $A_4$ are independently hydrogen, hydroxyl, halogen, $C_1$–$C_4$ alkyl, ethenyl, ethynyl, $C_3$–$C_6$ cycloalkyl, fluoromethyl, difluoromethyl, difluoroethyl, trifluoromethyl, hydroxymethyl, $C_1$–$C_{18}$alkoxy methyl, phenoxymethyl, $C_1$–$C_3$alkyl aminomethyl, $C_1$–$C_3$ dialkyl aminomethyl;
$R_8$ is hydrogen, hydroxyl, amine, $C_1$–$C_4$ alkoxy or aryloxy, —SH, $C_1$–$C_6$ thioalkyl or thioaryl;
$R_9$ is $C_1$–$C_4$ alkyl, $C_6$–$C_{12}$ aryl, alkylaryl, —($CH_2$)$_n$—$CO_2$-($CH_2$)$_m$—$R_{11}$, wherein $R_{11}$ is hydrogen, hydroxyl, methyl, alkyloxy, aryloxy or an amine, n is 0–4 and m is 0–4;
$R_{12}$ is hydrogen, CN, halogen, or $R_9$;
Z is a fluorine substituted carbon;
X is a carbon substituted with hydrogen, hydroxyl, cyano, nitro, halogen, $C_1$–$C_4$ alkyl, or an amine.

2. The compound of claim 1 wherein X is a fluorine substitute carbon atom.

3. The compound of claim 2 wherein $R_3$ is fluorine.

4. The compound of claim 1 wherein $R_8$ is methoxy and $R_9$ is a carbomethoxy group.

5. The compound of claim 1 which is
a) 2-(4-(1-cyclopropyl-3-carboxy-6,8-difluoro-1,4-dihydro-4-oxo-7-quinolinyl)-1-piperazinyl)-2-butenedioic acid, dimethyl ester;
b) 2-(4-(1-ethyl-3-carboxy-6-fluoro-1,4-dihydro-4-oxo-7-quinolinyl)-1-piperazinyl)-2-butenedioic acid, dimethyl ester;
c) 2-(4-(1-cyclopropyl-3-carboxy-5,6,8-trifluoro-1,4-dihydro-4-oxo-7-quinolinyl)-1-piperazinyl)-2-butenedioic acid, dimethyl ester;
d) 2-(4-(1-cyclopropyl-3-carboxy-6-fluoro-1,4-dihydro-4-oxo-7-quinolinyl)-1-piperazinyl)-2-butenedioic acid, dimethyl ester;
e) 2-(4-(3-carboxy-1-cyclopropyl-6,8-difluoro-1,4-dihydro-4-oxo-7-quinolinyl)-1-piperazinyl)-2-pentenedioic acid-(E)-1,5-dimethyl ester;
f) 2-(4-(5-amino-3-carboxy-1-cyclopropyl-6,8-difluoro-1,4-dihydro-4-oxo-7-quinolinyl)-1-piperazinyl)-2-butenedioic acid, (E)-1,4-dimethyl ester;
g) 2-(4-(3-carboxy-1-cyclobutyl-6,8-difluoro-1,4-dihydro-4-oxo-7-quinolinyl)-1-piperazinyl)-2butenedioic acid, (E)-1,4-dimethyl ester; or
h) 2-(4-(3-carboxy-1-benzene(4-fluoro)-6,8-difluoro-1,4-dihydro-4-oxo-7-quinolinyl)-1-piperazinyl)-2butenedioic acid, (E)-1,4-dimethyl ester.

6. A pharmaceutical composition comprising an antibacterially effective amount of a compound of Formula IA according to claim 1 in a mixture with a pharmaceutical carrier.

7. A method of treating bacterial infections in warm-blooded animals comprising administering to said animals an antibacterially effective amount of a compound of Formula IA in claim 1.

* * * * *

UNITED STATES PATENT OFFICE
CERTIFICATE OF CORRECTION

Patent No. 5,262,417    Dated November 16, 1993

Inventor(s) Ronald B. Gammill, Sharon N. Bisaha, Joseph M. Timko, Thomas M. Judge, Michael R. Barbachyn, Kyoung S. Kim It is certified that error appears in the above-identified patent and that said Letters Patent is hereby corrected as shown below:

On the cover page should have cross-references to related U.S. patent applications
--This application is the continuing national phase of international application PCT/US89/05213, filed 24 November 1989, which was a continuation in part of three US Patent applications: US Serial No. 07/411,449, filed 25 September 1989, abandoned, US Serial No. 07/355,016, filed May 22, 1989, abandoned and US Serial No. 07/335,163, filed 7 April 1989, abandoned. US Serial No. 07/355,016 was a continuation in part of US Serial No. 07/326,907 filed 22 March 1989, abandoned. US Serial No. 07/335,163 was a continuation in part of US Serial No. 07/280,603 filed 6 December 1988, abandoned.--

Signed and Sealed this

Thirteenth Day of December, 1994

Attest:

BRUCE LEHMAN

Attesting Officer    Commissioner of Patents and Trademarks